United States Patent [19]

Gardner, Jr. et al.

[11] Patent Number: 5,792,998
[45] Date of Patent: Aug. 11, 1998

[54] ACOUSTICAL HEARING PROTECTIVE DEVICES UTILIZING DYNAMICALLY STIFF FOAM AND METHODS OF PRODUCING SAME

[75] Inventors: Ross Gardner, Jr., Indianapolis; Gregory L. Simon, Zionsville, both of Ind.

[73] Assignee: Cabot Safety Intermediate Corporation, Southbridge, Mass.

[21] Appl. No.: 698,404

[22] Filed: Aug. 15, 1996

Related U.S. Application Data

[60] Continuation-in-part of Ser. No. 450,122, Oct. 6, 1995, abandoned, which is a division of Ser. No. 48,722, Apr. 19, 1993, Pat. No. 5,420,381.

[51] Int. Cl.⁶ ............................................. H04R 25/00
[52] U.S. Cl. ........................................... 181/130; 181/135
[58] Field of Search ............................. 181/129, 130, 181/131, 135, 137; 128/864, 865, 866, 867; 2/209; 381/187, 188, 205

[56] References Cited

U.S. PATENT DOCUMENTS

| | | | |
|---|---|---|---|
| Re. 29,487 | 12/1977 | Gardner, Jr. | 128/864 |
| 2,801,423 | 8/1957 | Shaw et al. | |
| 3,016,054 | 1/1962 | Rosenblatt | 128/866 |
| 3,377,296 | 4/1968 | Dwyer | 521/137 |
| 4,260,575 | 4/1981 | Thew et al. | |
| 4,461,290 | 7/1984 | Gardner, Jr. et al. | 128/864 |
| 4,465,159 | 8/1984 | Stallings | |
| 4,471,496 | 9/1984 | Gardner, Jr. et al. | |
| 4,490,857 | 1/1985 | Leight et al. | 2/209 |
| 4,517,150 | 5/1985 | Harashima et al. | |
| 4,671,265 | 6/1987 | Andersson | 128/864 |
| 4,682,374 | 7/1987 | Geiser | |
| 4,819,624 | 4/1989 | Leight et al. | 128/866 |
| 4,864,610 | 9/1989 | Stevens | 181/135 X |
| 4,958,697 | 9/1990 | Moody | |
| 4,970,243 | 11/1990 | Jacobs et al. | |
| 5,038,412 | 8/1991 | Cionni | |
| 5,148,887 | 9/1992 | Murphy | |
| 5,188,123 | 2/1993 | Gardner, Jr. | 128/864 |
| 5,203,352 | 4/1993 | Gardner, Jr. | |

FOREIGN PATENT DOCUMENTS

| | | |
|---|---|---|
| WO 95/34589 | 12/1995 | WIPO |
| WO 95/34590 | 12/1995 | WIPO |

*Primary Examiner*—Khanh Dang
*Attorney, Agent, or Firm*—Fishman, Dionne, Cantor & Colburn

[57] ABSTRACT

An earmuff cushion and other foam hearing protective components such as earplugs and pods for semi-aural hearing protectors and earplugs providing improved attenuation are described. The cushion and other foam hearing protective components are comprised of a dynamically stiff foam material having a low static stiffness, and a high dynamic stiffness, which produces improved attenuation in the earmuff and other hearing protective devices in which it is used. Earmuffs made from the cushion, semi-aural hearing protectors, earplugs, and improved methods of making the hearing protective devices are also described.

57 Claims, 25 Drawing Sheets

ACOUSTICAL HEARING PROTECTIVE DEVICES UTILIZING DYNAMICALLY STIFF FOAM AND METHODS OF PRODUCING SAME

CROSS-REFERENCE TO RELATED APPLICATION

This is a continuation-in-part of application Ser. No. 08/450,122 filed Oct. 6, 1995 now abandoned, which, in turn, is a divisional of application Ser. No. 08/048,722 filed Apr. 19, 1993, now U.S. Pat. No. 5,420,381.

TECHNICAL FIELD

The field of art to which this invention pertains is hearing protection and hearing protective devices, specifically circumaural bearing protectors (acoustical earmuffs), semi-aural hearing protectors which cap or partially enter the ear, and aural hearing protectors (earplugs).

BACKGROUND ART

The specifications of commonly assigned application Ser. No. 08/450,122, now abandoned and U.S. Pat. No. 5,420,381 are incorporated herein by reference.

The use of earplugs, semi-aural hearing protectors, and earmuffs are the most useful ways to protect against hearing loss in those environments where noise levels are not controllable within safe limits. Where the use of earplugs is either impossible or impractical, the use of semi-aural hearing protectors or earmuffs provides a means of reducing sound intensity, in many instances to a degree even greater than that provided by the use of earplugs. Other uses for noise-excluding bearing protectors include producing quiet for study, sleep, or audio purposes. For audio purposes, a sound conducting duct or other communication device may be built into the hearing protector.

Earmuffs have advantages for intermittent use where continuous insertion and removal of earplugs would be annoying or impractical. Also, earmuffs tend to deliver higher in-field noise protection in many high frequency noise environments than most earplugs. Additional preference for earmuffs include use outdoors in cool weather and use in dry climates.

Semi-aural (also known as semi-insertable) hearing protectors generally protect similarly to earplugs, but usually to a lesser level. Semi-aural hearing protectors which enter the ear canal to a greater degree offer better protection but are somewhat less comfortable than those which simply cap the ear. Products which cap the ear have some of the attributes of both earplugs and earmuffs. Typically, they are used for intermittent noise exposures where lighter weight and improved low frequency attenuation are desirable.

Earplugs are generally preferred for continuous use over longer periods of time. Slow recovery foam earplugs such as those disclosed in U.S. Pat. No. Reissue. 29,487 are not only comfortable, but have also been shown to deliver high in-field noise protection at all frequencies.

All hearing protector products need to form a seal against the head or ear canal in order to be effective. Lower frequency attenuation for all three product types is affected by the dynamic stiffness of the flesh/protector interface. The present invention addresses products and processes whereby a dynamically stiff foam is produced which is stiff at frequencies of interest for hearing protectors but which is statically very soft, thereby allowing ease of sealing against the head or ear canal. At low frequencies, up to about 1000 Hz, all hearing protectors are stiffness controlled, which extends up to about 250 Hz for earmuffs and up to 1000 Hz for semi-aural devices and earplugs. Generally, earmuffs have poorer low frequency attenuation values than earplugs. Part of the problem is because at lower frequencies of 125 to 1000 Hz the earmuff vibrates upon the earmuff cushion and flesh in a pumping mode. To a point where the flesh controls motion, the cushion component of the earmuff controls low frequency attenuation. Most cushions are selected of a soft combination of materials to achieve conformation to the head about the ear and claim comfort because of this ease of conformation. Semi-aural devices and earplugs are also stiffness controlled at previously defined frequencies up to 1000 Hz and sometimes at higher frequencies, especially 2000 Hz. Again, the stiffness of the semi-aural pod or earplug along with the contacted flesh controls the low-frequency motion of the device. Hearing protectors of these general types comprising dynamically stiff foam would all be expected to yield improved low frequency sound attenuation. As used herein, "dynamically stiff" refers to foams having a low static stiffness and a high dynamic stiffness.

Most earmuffs are made up of a band section, a cup section, and a cushion section. The band section extends between the pair of muffs, and holds the muffs snugly against the head of the wearer. The cup section is typically filled with foam material, and in this combination of cup and foam is where the sound attenuation takes place. The cushion section extends around the edge of the cup, and this cushion serves two purposes, to provide comfort to the wearer, and to form a seal to assist in keeping unwanted noise away from the wearer's ears.

There is a constant search for ways to improve the comfort, sound attenuation characteristics, appearance and designs of these earmuffs (note, for example, U.S. Pat. Nos. 2,801,423; 4,260,575; 4,465,159 to Stallings; U.S. Pat. No. 4,471,496; and 4,682,374). In one of these, U.S. Pat. No. 2,801,423 to Shaw, the cushion comprises a covering of pliable or flexible but non-elastic material which forms a chamber around the periphery of the rigid cup. This chamber is substantially gas evacuated and partially filled with a liquid.

Shaw et al. later redefines the preferred wall material as being polyvinyl chloride having a wall thickness of about 0.005 to about 0.01 inch and/or a dynamic Young's modulus of about $5 \times 10^3$ p.s.i. FIG. 1 shows the typical attenuation achieved by an adaptation of this patent. The figure shows ANSI S3.19 Real ear attenuation vs. Calculated Attenuation (C) for Safety Supply Model 258 Ear Muffs (Liquid Cushions as per U.S. Pat. No. 2,801,423).

The broken line on the graph indicates the calculated values and the solid line the real ear values. Depths of 0 are formulated by the following formula:

| | |
|---|---|
| $F_O = A_2/VM \times 35460$ | where $A = 72.84$ cm$^2$ |
| | $V = 189.90$ cm$^3$ |
| | $M = 116.08$ g |
| $F_O = 92$ Hz | |

Semi-aural (semi-insertable) hearing protectors fall generally into three categories, including protectors that cap the entrance to the ear canal; protectors which enter the ear canal and seal the ear canal prior to the bend in the ear canal (usually referred to simply as semi-aural devices); and protectors that enter the ear canal and take the bend in the ear canal (sometimes referred to as banded earplugs). As used herein, "semi-aural hearing protectors" refers generally to any hearing protector falling into one of the three categories described above. FIGS. 23 and 24 show the manufacturer's attenuation data for commercially-available semi-aural devices which enter the ear (FIG. 23) and commercially-available semi-aural devices which cap the ear (FIG. 24).

A typical semi-aural hearing protector assembly generally comprises a resilient U-shaped band with holders at either end, and a pair of inwardly directed ear protectors ("pods") that are detachably mounted to the holders. Attenuation for semi-aural hearing protectors generally increases as entry into the ear canal increases. However, comfort is inverse to attenuation, with comfort increasing as entry into the ear canal decreases. Thus there is apparently no commercially viable banded earplugs (i.e., semi-aural hearing protectors designed to take the bend of the ear canal) available which are comfortable enough for widespread use.

Furthermore, little prior art describing the use of foam in any semi-aural hearing protectors exists. In U.S. Pat. No. 4,461,290 to Gardner et al., pods are described comprising foam E-A-R® Plugs rolled down and inserted into a capsular element. Semi-aural devices are also described in U.S. Pat. No. 4,490,857 to Leight et al., wherein reference is made to the use of foam formulations based on U.S. Pat. No. Reissue 29,487 to Gardner.

U.S. Pat. No. 5,188,123 to Gardner describes a protective earplug including a stem which permits alternative push-in and roll-down modes of insertion. The earplug includes a soft, smoothly contoured foam main body element comprising a resilient, homogenous viscoelastic polymer foam. The main body element further comprises a manipulable stem axially embedded therein and extending outwardly form its base.

Foam earplugs are also described in U.S. Pat. No. 5,203,352 to Gardner, which discloses that where the room temperature recovery time of the nose section of the claimed earplug is greater than about 60 seconds, and the body temperature recovery time in minutes multiplied by the density (in pounds per cubic foot) squared is greater than about 40, it appears that the properties exhibited by such temperature-dependent viscoelastic polymeric foam material results in improved attenuation of the earplug hearing protector in the lower range of audible frequencies (ca. 125–1000 Hz). Resilient polymeric foam earplugs consisting solely of a nose section comprised of such a polymeric foam material exhibiting the above-mentioned low-frequency attenuation benefits is described in Example 3 (column 14, lines 9–65) of the patent. Such earplugs consist of a foam made from 150 parts HYPOL® 3000 (available form W. R. Grace Co.) polyetherpolyurethane prepolymer and 225 parts UCAR® 154 (available from Union Carbide Corp.) acrylic latex, and cured at laboratory temperature and have the following physical properties:

| | |
|---|---|
| Weight, g | 0.4050 |
| Length, inches | 0.741 |
| Diameter, inches | 0.532 |
| Apparent density, lbs/ft³ | 9.39 |
| Recovery time at 70–72° C., sec | 77.3 |
| Recovery time at 96° C., sec | 37.2 |
| Nose first touches at 96° C., sec | 13.3 |
| Equilibrium pressure, psi | 0.69 |

Thus the foam of this patent is a hydrophilic slow recovery foam formed from HYPOL polyether polyurethane prepolymers, acrylic-containing polymers, and water. The slow recovery of the foam is due to the acrylic polymer employed, which dominates the properties of the foam. U.S. Pat. No. 4,725,627 to Arnason and Kunke refer to this acrylic polymer as a recover rate modifier or "tackifier" and state that their belief is that the cell walls in the product (a toy) are held together by the tackiness of the modifier until the compressive recovery strength of the foamed polyurethane is greater than the adhesive bond between the cell walls due to the presence of such a modifier. Whether slow recovery is due to tack or not, it seems undisputed that the slow recovery is attributable to the acrylic polymer rather than the polyurethane. Furthermore, the foam of U.S. Pat. No. 5,203,352 has an isocyanate index of 1.0 upon drying, due to the reaction of excess isocyanate groups in the HYPOL with only water.

While previous hearing protective devices have been suitable for many uses, they still possess certain drawbacks and disadvantages, one of these being decreased attenuation at lower frequencies. The present invention is directed to not only products but materials and methods for producing foam components for hearing protectors which address the above concerns.

SUMMARY OF THE INVENTION

The present invention is directed to foam components for hearing protectors, i.e., earmuff cushions, pods, and earplugs which provide improved attenuation and ease of manufacture. The foam components are made up of a foam material which has a low static stiffness, and a high dynamic stiffness. This invention simplifies construction which contributes to its ease of manufacture, retains ease of conformation about the ear and this same material acts dynamically very stiff reducing the motions of the earmuff cup and other parts of hearing protectors.

Another embodiment of the invention is an acoustical earmuff device containing such cushions, a semi-aural device containing such pods, and earplugs.

Yet another embodiment of the invention is a method of making such cushions, pods, and earplugs, through molding them by passing the ingredients through a mix/meter machine into a mold, optionally followed by crushing the molded item to prevent puckering or to provide increased deflection characteristics while maintaining dynamic stiffness.

Dynamically stiff cushions made by the above process when placed on low to medium volume earmuffs, the preferred types, on semi-aural devices, and used with earplugs lead to dramatically improved attenuation results. These results for the earmuff cushions exceed those predicted by equations normally employed for calculation purposes.

These, and other aspects of the invention will become apparent from the following detailed description.

DETAILED DESCRIPTION OF THE INVENTION

Figure 1:
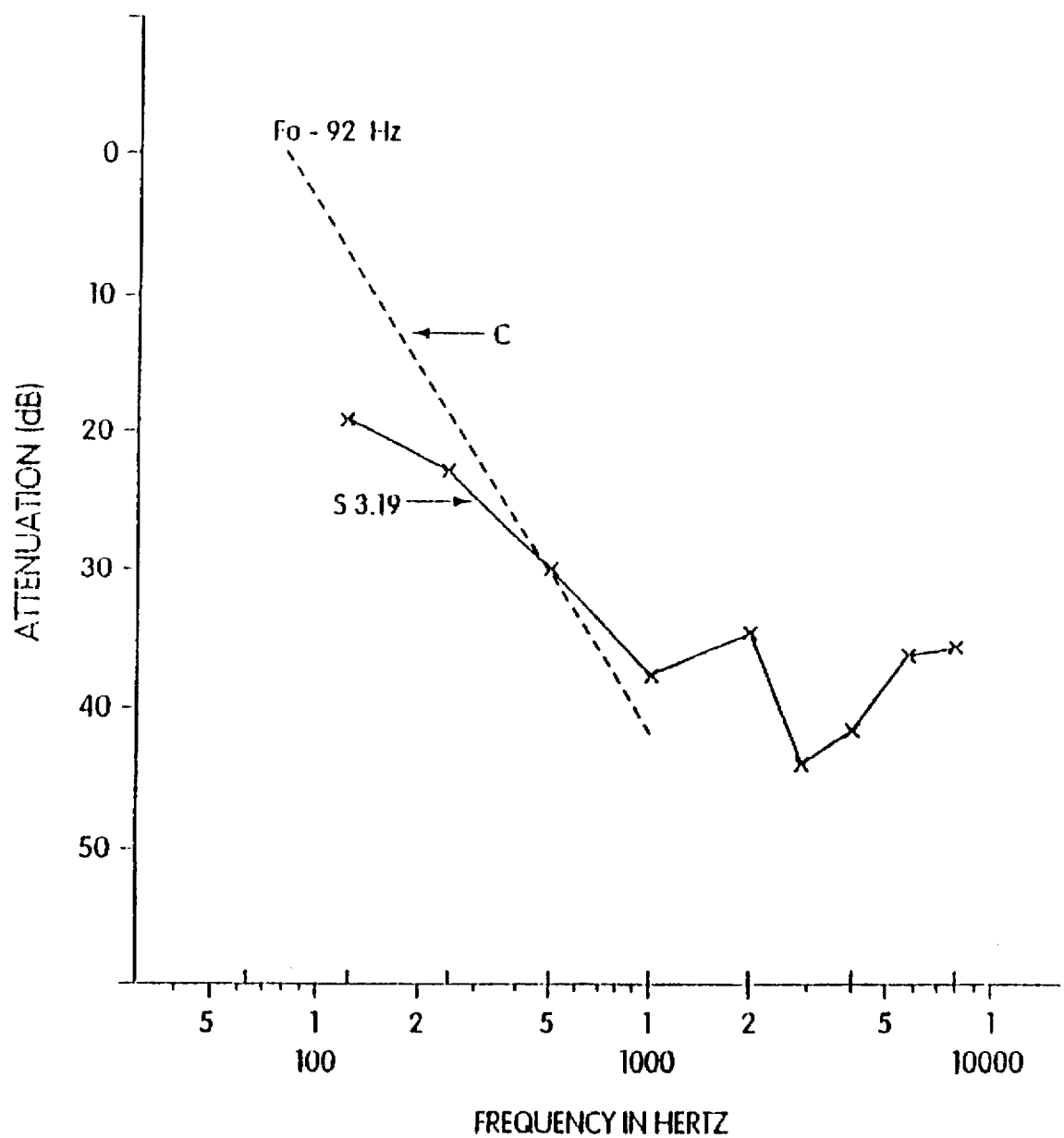
FIG. 1 shows typical attenuation of earmuff cushions of the prior art.

The critical component of the foam components which provide the improved attenuation in the earmuff and other hearing protective devices is its dynamic stiffness characteristics. The term "dynamically stiff" foam as used herein refers to a foam material having a low static stiffness and high dynamic stiffness, thereby providing improved attenuation for hearing protectors using the same. The degree of stiffness desired is dependent upon the ability of the cushion to form an acoustical seal against the head or ear part. It has been found that material with a low static stiffness, and high dynamic stiffness, provide improved attenuation according to the present invention. These stiffness characteristics are defined in terms of dynamic complex spring constant (K*), static spring constant ($K_s$), and dynamic material loss factor ($\eta$).

In order to provide the improved attenuation according to the present invention it is important that the foam parts have a dynamic spring constant of at least about 300 pounds/inch and a dynamic material loss factor of at least about 0.25, as measured by the methods disclosed herein, and preferably a dynamic spring constant of at least about 1,000 pounds/inch. It is also important that the material have a static spring constant of up to about 60 pounds/inch, as measured by the methods disclosed herein, and preferably up to about 30 pounds/inch. Preferably, the foam has a density of about 5–20 pounds per cubic foot, and most preferably a density of about 7–15 pounds per cubic foot.

While the cushions and other foam components according to the present invention can be made of any polymeric material having the above described stiffness characteristics, polyurethane material has been found to be particularly suitable, for example, because of its stability in the presence of skin oils. And while any moldable polyurethane can be used, an especially preferred material is that described in U.S. Pat. No. 3,377,296 to Dwyer, the disclosure of which is herein incorporated by reference.

Polyurethane Formulations

The preferred polyurethane is diisocyanate based, preferably reacted with polyols with a portion thereof being at least tri-functional, and has an isocyanate index of less than about 0.9.

According to Immergut and Mark (Plasticization and Plasticizer Processes, American Chemical Society Publications);

"Plasticization, in general refers to a change in the thermal and mechanical properties of a given polymer which involves: (a) lowering of rigidity at room temperature; (b) lowering of temperature, at which substantial deformation can be effected with not too large forces; (c) increase of elongation to break at room temperature; (d) increase of the toughness (impact strength) down to the lowest temperature of serviceability. These effects can be achieved: (1) by compounding the given polymer with low molecular weight compound or with another polymer; and (2) by introducing into the original polymer a comonomer which reduces crystallizability and increases chain flexibility."

Plasticizers have been categorized into two types, internal plasticizers and external plasticizers. Internal plasticizers are actually a part of the polymer molecule—e.g., a second monomer is copolymerized into the polymer structure thereby making it less ordered, and therefore, more difficult for the chains to fit closely together. This softens the polymer—i.e., lowers the glass transition temperature (Tg) or the modulus. Usually, the internal plasticizer is a monomer whose polymer has good low temperature properties.

External plasticizers are compounds mixed in with the polymer which make it more difficult for the chains to fit closely together. This softens the polymer—e.g., lowers the Tg or the modulus. External plasticizers are often categorized as primary or secondary, defining the degree of compatibility or in terms of its efficiency or permanence.

Polyurethanes are typically block co-polymer consisting of polyester polyols and/or polyether polyols reacted with isocyanates having a functionality of 2 or more. Sometimes the term polymers of isocyanates is used to better define systems where water or amine terminated compounds are reacted resulting in polyureas. Here polyurethane will be used all-inclusively.

When using a polymer polyol as a reactant, it is a plasticizer. Generally, the larger the polymer chain lengths for a particular type polyol the lower the Tg obtained. Types of polyols could also be referred to as having different efficiencies, with polyethers being more efficient than polyesters. Likewise, polyols could be considered more efficient than polyamines.

Monofunctional reactants produce side chains which act as plasticizers. However, they may be more or less efficient than the plasticizer they replace. External plasticizer may be employed in polyurethane. Compatibility is quite important here and often a preferred approach has been to "under index" the system. The best way of ensuring compatibility is to use segments of the polymer itself as plasticizer.

"Underindexing" is the in situ production of external plasticizer while at the same time producing more dangling polymer segments. Underindexing is not new to the art and was used in the early 1960s to produce soft foams for use in mattresses and the like. See, e.g., U.S. Pat. No. 3,377,296 and *Cellular Plastics—Today's Technology*, Apr. 24–25, 1963, "Technology of Super Soft Flexible Urethane Foams" by Dwyer, Kaplan, Pirer and Stone.

The cushions, pods, earplugs or other hearing protective foam components according to the present invention use di- and tri-functional polyether polyols of varying molecular weight, underindexing and density adjustments as methods of formulating compositions which produce molded, dynamically stiff, noise excluding earmuff cushions, and other hearing protective foam components. At least a portion of the polyol used should have tri-functionality (so as to produce a solid foam as opposed to simply a liquid polyurethane). Surfactant combinations are employed to maintain closed cells, a requirement for noise excluding foams. Surfactant/oil combinations may also be used, wherein the ratio of surfactant:oil is adjusted so as to aid in controlling cell strength and degree of reticulation. Preferably, the oil is a polysiloxane. An acrylic latex may be used to introduce a water blowing agent. Additional optional additives include, but are not limited to, catalysts, fillers, plasticizers, colorants, antifoam agents, fire retardants, cell stabilizers, cell regulators, chain extenders, hindered amine light stabilizers and internal mold release agents. Lowering of the isocyanate index (NCO/OH) results in softening, as does increasing polyol chain segment length.

Earmuff Cushions and Earmuffs

The earmuff cushions of the present invention provide improvement in attenuation both in use with the standard types of earmuffs generally on the market and without the bladders currently used.

Figure 2:
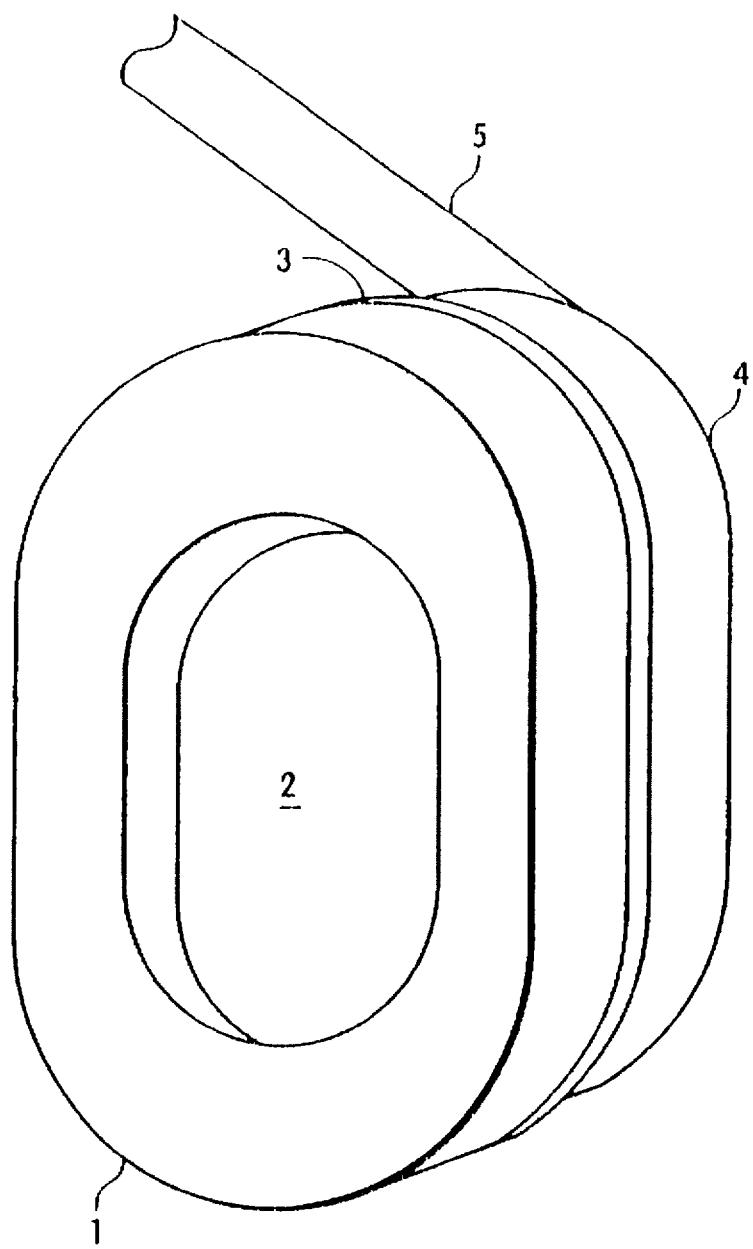
FIG. 2 shows a standard earmuff containing a cushion according to the present invention.

As shown in FIG. 2, the cushion 1 is attached to the seal plate 3, typically by a conventional pressure adhesive such as an acrylic material (not shown). The seal plate is similarly attached to the cup 4, again by conventional methods such as ultrasonic welding. The headband 5 is attached to the cup, by typical mechanical means such as through a grommet (not shown), e.g., like those used in the conventional E-A-R® 1000–3000 Model earmuffs produced by Cabot Safety Corporation, Indianapolis, Ind. The foam liners 2 lining the inner surfaces of the cup 4 can be made of conventional open cell foam materials, such as conventional polyurethanes as are currently used. Elimination of the cushion bladder provides the advantages of material savings and labor savings, in addition to the increased attenuation. Although the foam according to the present invention can be used inside a conventional bladder system and some of the attenuation advantages of the present system realized, the manufacturing advantages would not be realized.

It may also be preferred to mold the foam part inserts of the earmuff onto other components of the earmuff such as seal plates or seal plate components.

Semi-Aural Hearing Protectors

As used herein, "semi-aural hearing protector" refers generally to the entire class of semi-aural devices, including but not limited to hearing protectors that cap the entrance to the ear canal, protectors that enter the ear canal and seal the ear canal prior to the bend in the ear canal, and protectors that enter the ear canal and take the bend in the ear canal. Semi-aural hearing protectors generally comprise a U-shaped flexible band and two pod assemblies for providing sound attenuation, as will be described in more detail below. A particularly preferred embodiment further comprises a stem or stiffener disposed within the foam component of each pod assembly. In an alternative embodiment, the foam component of each pod may further comprise a slippery outer surface for ease of insertion, for example a polyurethane coating. In yet another embodiment, the foam component of each pod may be embossed after molding.

Figure 17A:
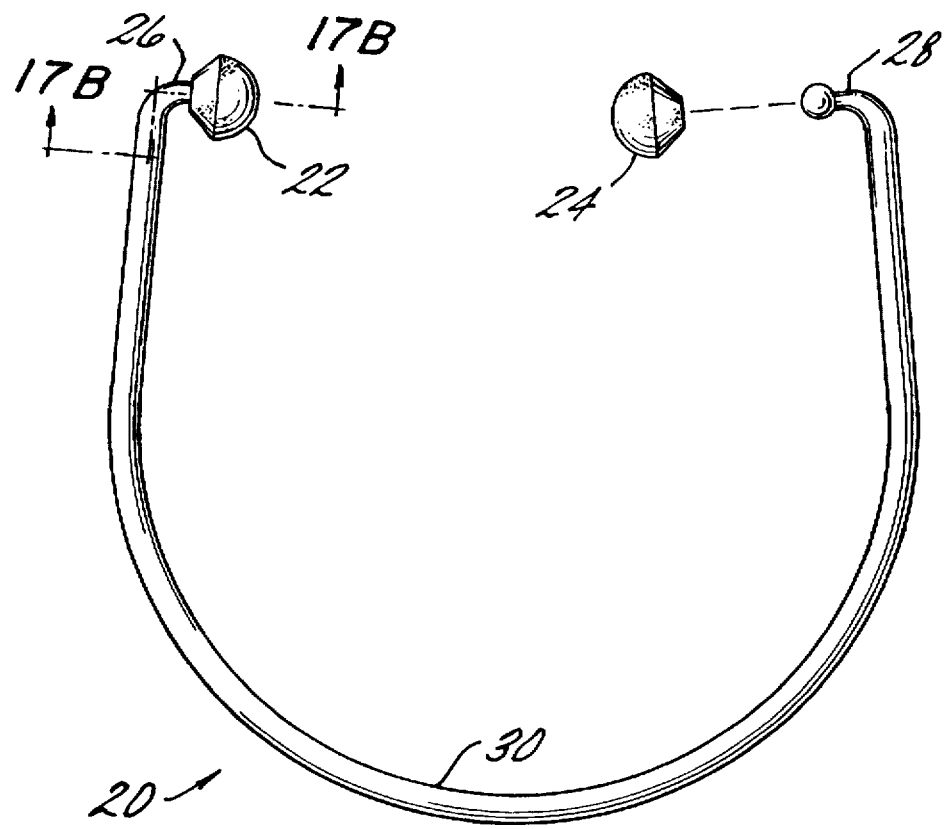
FIG. 17A shows a standard semi-aural device containing foam caps according to the present invention.
Figure 17B:
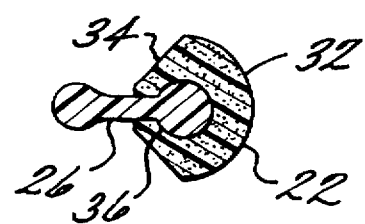
FIG. 17B is a cross-sectional view of the foam component shown in FIG. 17A.

Referring now to FIGS. 17A–B, a semi-aural hearing protector designed to cap the ear is shown generally at 20. Hearing protector 20 has two dynamically stiff foam pod components 22, 24 snapped onto generally conical or hemispherical ends 26, 28 of a generally U-shaped under-the-chin band 30. In another embodiment of the present invention, it may be preferred to mold the foam components 22, 24 directly onto the ends of band 30. In a preferred embodiment, foam components 22, 24 have a forward generally hemispherical portion 32 for contact with the ear, or any other shape suitable to optimize contact with the ear. A generally conical back portion 34 forms an internal recess 36 for receiving ends 26, 28 in snap-in fashion. As the size of the forward portion 32 of the dynamically stiff foam component 22, 24 is increased within the size limitation of the concha, increased attenuation and increased comfort result.

Figure 18A:
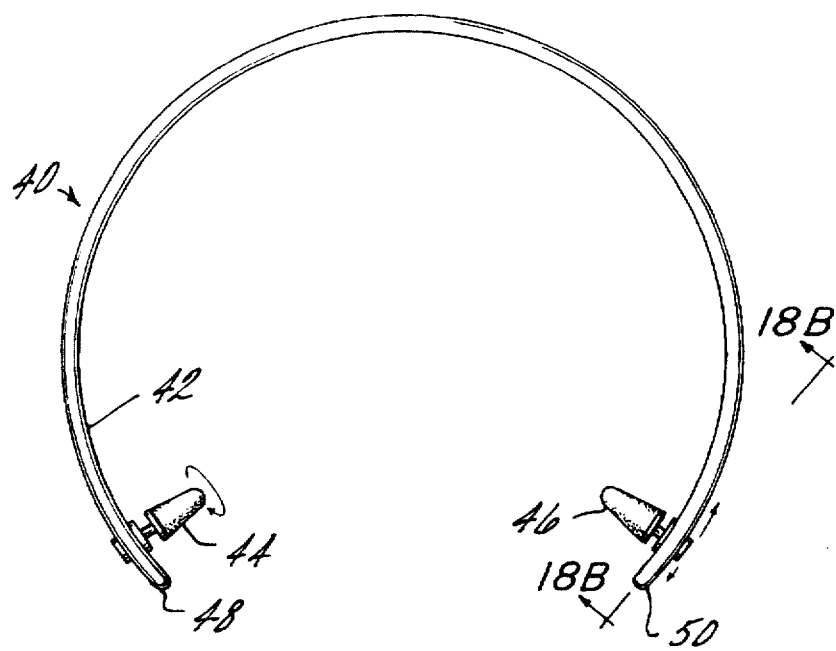
FIGS. 18A–C show alternative embodiments of standard semi-aural devices containing foam pods according to the present invention.
Figure 18B:
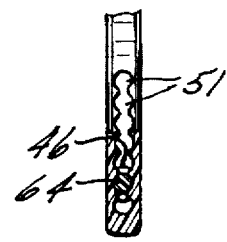

Preferred embodiments of semi-aural devices of the present invention which enter the ear canal and seals the ear canal prior to the bend in the ear, or which enter the ear canal and go beyond the bend of the ear canal, are shown at FIGS. 18A–F. Referring to FIG. 18A and FIG. 18B, an exemplary semi-aural device of this type 40 includes a headband 42 and a pair of rotatable pods 44, 46 attached to opposite ends 48, 50 of headband 42. As shown in FIG. 18B, ends 48, 50 define a series of connected openings 51 whereby pods 44, 46 may be adjusted along the length of headband 42 for the wearer's comfort.

Figure 18C:
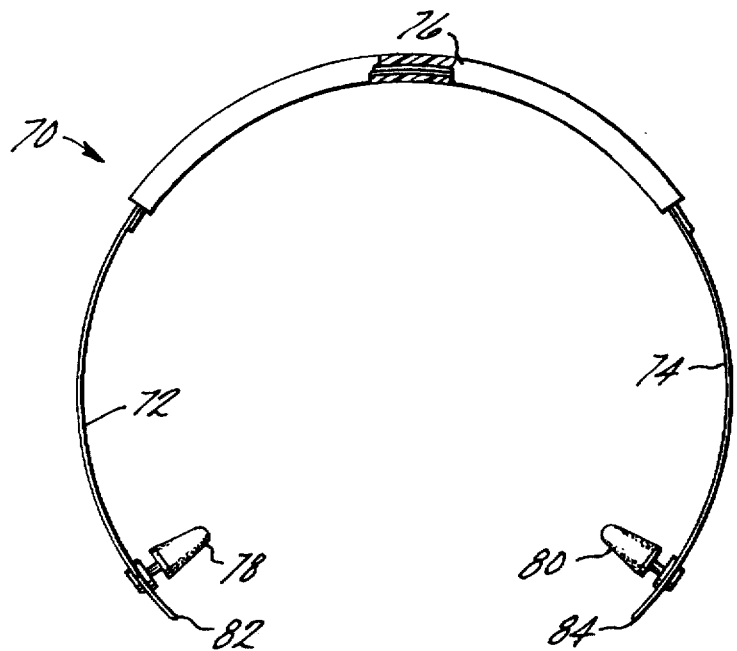

FIG. 18C depicts another embodiment of a semi-aural device of the present invention, comprising headband 70, which consists of arc-shaped parts 72, 74 slidably joined by means well-known in the art 76. In this embodiment, pods 78, 80 are permanently affixed to ends 82, 84 of arc-shaped parts 72, 74 by means well known in the art. This design reduces rubbing noise.

Figure 18D:
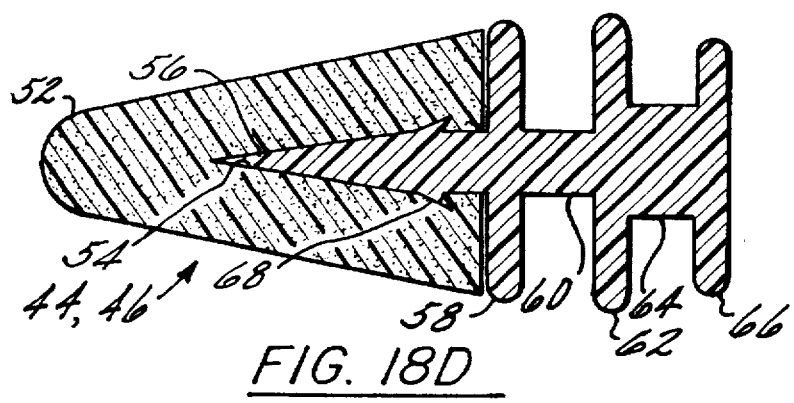
FIGS. 18D–F show cross-sectional views of pods for the semi-aural devices according to the present invention.
Figure 18F:
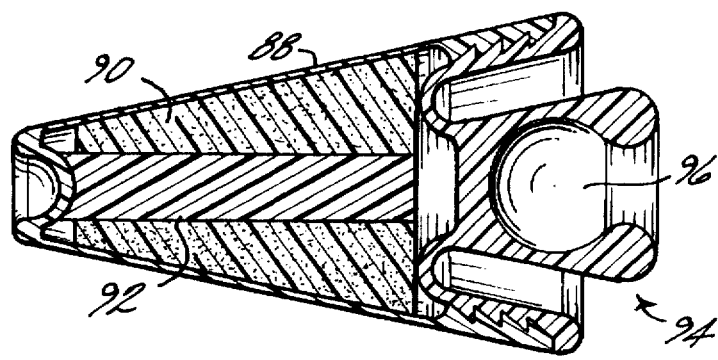

Pods 44, 46, for example, are shown in greater detail in FIG. 18D, wherein pods 44, 46 comprise a generally hemispherical or conical dynamically stiff foam component of the present invention 52 containing a recess therein 54 for receiving a stiffening member or stem 56. The stem comprises a first flange 58 for retaining the foam component 52, a narrower stem portion 60 for rotation, a flange 62, and a wider stem portion 64 and third flange 66 for retention to headband 42 and adjustment along the headband through interconnected openings 51. In addition, flange 68 may aid in retention of the foam component. While the above-described means of pod attachment to the band are preferred, any suitable means well-known in the art may be used. For example, FIG. 18F is a cross-sectional view of a pod attachable by snap-on means. A slippery outer coating 88 surrounds dynamically stiff foam component 90 and stem 92. Attachment means 94 contains recess 96 for retention on the end of a band comprising a larger generally hemispherical or conical portion such as portion 28 shown in FIG. 17A.

Figure 18E:
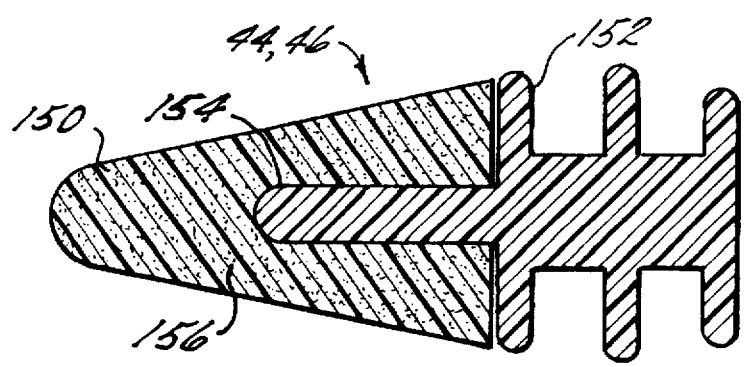
Figure 21:
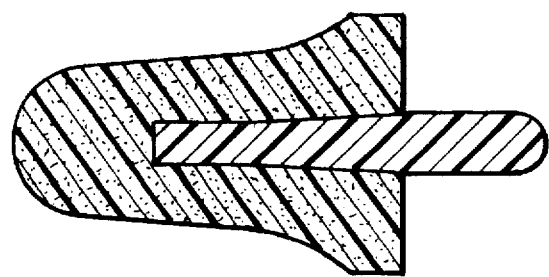
FIG. 21 is a sectional view of an earplug with a stiffening member according to the present invention.

An alternative embodiment of pods 44, 46 is shown in FIG. 18E, wherein the dynamically stiff foam component 150 is directly molded onto stem component 152. The tip 154 of the stem component 152 acts as a stiffener. The stiffener acts to pull foam into the ear to maximize attenuation. In order to fit all or most ear canals, the length of the foam component 156 from about the tip 154 to the forward end of the pod inserted into the ear is preferably about 0.25 inches and the pod diameter at the stem tip 154 is preferably above about 0.46 inches. These dimensions will enable a comfortable fit even for those persons with difficult-to-fit ear canals (about one out ten users). These dimensions are also suitable for use with various-shaped stiffeners, for example, the stiffener shown in FIG. 18D. In lieu of the above preferred foam dimensions, different sizes of pods may also be utilized to fit ear canals of different sizes.

For optimum attenuation performance of semi-aural devices having foam components, the preferred stiffening member is a stem having a tip of increased bendability. This increased bendability can be accomplished by a decrease in durometer of the stem or a decrease in the cross-sectional dimension of the stem. This increase in stem tip flexibility has been found to be a necessary requirement for the comfort of those wearers having fairly sharp bends in the ear canal. While the dynamically stiff foam of the present invention is suitable for use in semi-aural devices with a stiffener, other foams may also be used.

Figure 25:
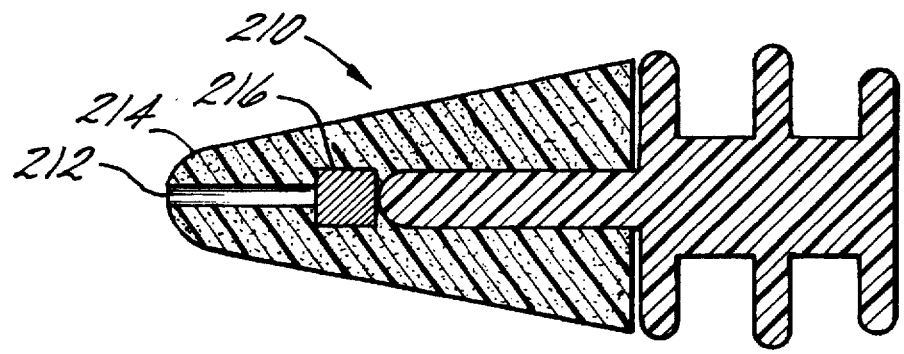
FIG. 25 is a sectional view of a pod assembly having means for transmitting sound to the ear according to the present invention.
Figure 26:
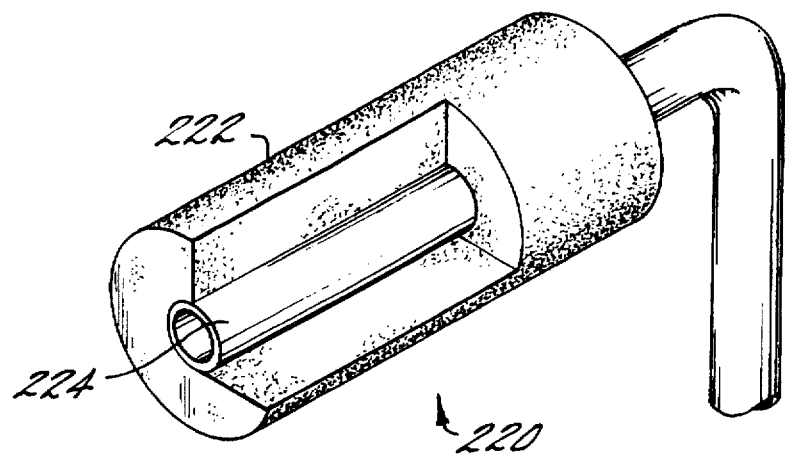
FIG. 26 is a sectional view of a pod assembly having a hollow stem for transmitting sound to the ear according to the present invention.

Referring now to FIGS. 25 and 26, yet another alternative embodiment of the semi-aural devices of the present invention is shown, wherein sound may be received by the wearer. In FIG. 25, pod 210 is coaxially bored to form an opening 212 through the length of tip 214. Sound from a transceiver 216 may then be received by the wearer through longitudinal bore 212. Alternatively, as shown in FIG. 26, foam component 222 of pod 220 is coaxially bored throughout its length. The end 224 of a hollow headband is inserted therein. The headband is part of a headphone for conducting sound to the wearer through the longitudinal bore of the headband.

Figure 19:
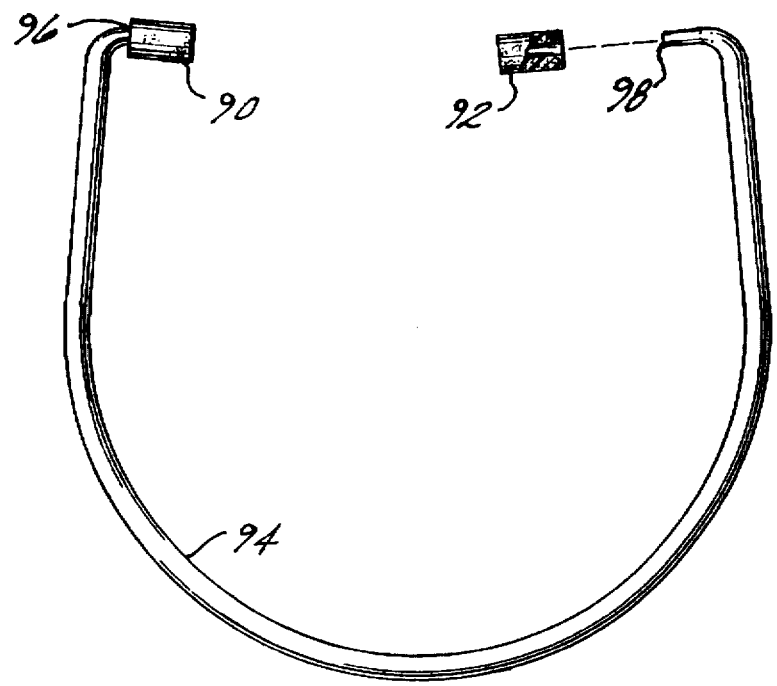
FIG. 19 shows standard banded earplugs comprising foam earplugs according to the present invention.

Referring now to FIG. 19, a preferred semi-aural hearing protector of the present invention is shown wherein the foam component enters the ear canal past the bend in the ear canal. Foam earplug components 90, 92 are attached to a flexible under-the-chin band 94 at hemispherical ends 96, 98 through snap-on means. In another preferred embodiment of the present invention, it may be preferred to mold the foam part of the earplug directly onto the ends 96, 98 of band 94.

Earplugs

Figure 20A:
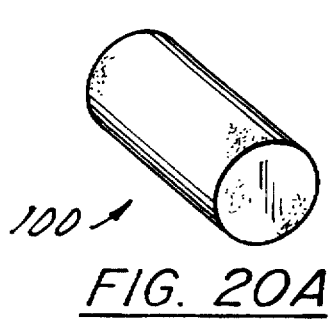
FIGS. 20A–D show alternative embodiments of foam earplugs according to the present invention.
Figure 20B:
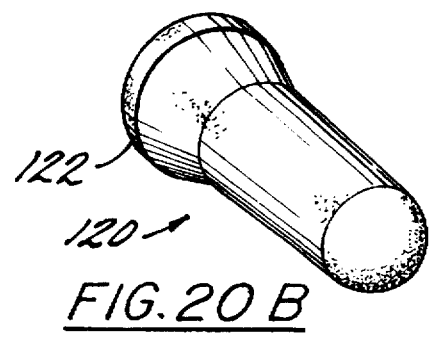
Figure 20C:
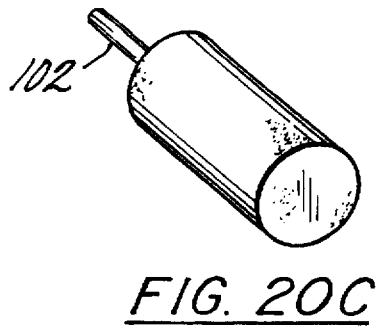
Figure 20D:
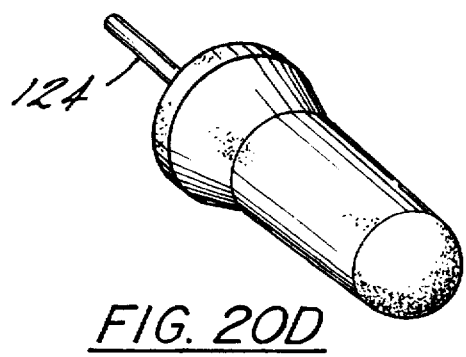

Referring now to FIGS. 20A–D, typical earplugs of the present invention are shown. Earplug shapes are well known in the art. One shape is a cylindrical foam hearing protector 100 as shown in FIG. 20A. Such an earplug may also comprise a stiffening member or stem 102 as shown in FIG. 20C. A particularly preferred embodiment is the cylindrical shape 120 with flared end 122 as shown in FIG. 20B. This earplug may also contain a stiffening member or stem 124 as shown in FIG. 20D. In one embodiment of the present invention, it may be preferred to mold the foam part of the earplug directly onto the stem or other stiffening members.

The foam ahead of the stem at the forward tip of the earplug is preferably about 0.25 inches and the earplug diameter at the stem tip is preferably about 0.46 inches or larger. In lieu of the above preferred foam dimensions, different sizes of earplugs may also be utilized to fit ear canals of different sizes. As with semi-aural hearing protectors, the preferred stiffening member is a stem having a tip of increased bendability. This increased bendability can be accomplished by a decrease in durometer or a decrease in the cross-sectional dimension of the stem. This increase in stem tip flexibility has been found to be a necessary requirement for the comfort of those wearers having fairly sharp bends in the ear canal.

Other preferred embodiments include a slippery outer surface on the earplug, thereby aiding the earplug device to slide by the ear canal, and an embossed surface on the earplug.

Figure 27:
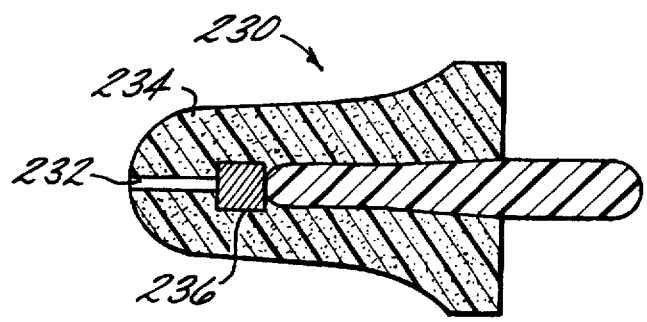
FIG. 27 is a sectional view of earplug having a means for transmitting sound to the ear according to the present invention.
Figure 28:
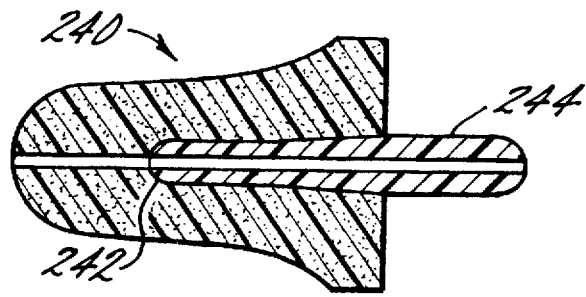
FIG. 28 is a sectional view of an earplug having a hollow stem for transmitting sound to the ear according to the present invention.

Referring now to FIGS. 27 and 28, yet another alternative embodiment of the earplugs of the present invention is shown, wherein sound may be received by the wearer. In FIG. 27, earplug 230 is coaxially bored to form an opening 232 through the length of tip 234. Sound from a transceiver 236 may then be received by the wearer through longitudinal bore 232. Alternatively, as shown in FIG. 28, earplug 240 is coaxially bored through its length. The end 242 of a hollow stem 244 is inserted therein. Hollow stem 244 may be attached to wire or headphone means for transmitting sound to the wearer through the bore of the hollow stem 244.

Method of Manufacture

The method for making the cushions and earplugs according to the present invention can be described by reference to FIG. 3. The reactants listed in Table 1 are mixed in conventional mixing equipment. This foam reaction mixture can be premixed and introduced into the mold or mixed as separate reactant streams and injected as a single stream directly into the mold, which may be preheated. "Injection" as used herein refers to mixing and introduction, or laying down of a stream under a given line pressure. For example, in a conventional mix/meter molding apparatus, at least two streams are mixed, and then introduced into the preheated mold, causing foaming to take place. Preferably, the contact mold surface is polypropylene, a copolymer of polypropylene or a mixture thereof The injection can take place at low or high line pressures ranging from, for example, about 20 to about 300 pounds per square inch. A liner or other hearing protector device component may be placed in the mold before injection in order to mold the foam component directly thereto.

The temperature is allowed to remain sufficiently high to cure the foam in the shape of the cushion or earplug, and then the molded article is removed from the mold. Preferably, the mold release agent consists of an oil-wax mixture dissolved or suspended in a suitable medium. Alternatively, the foam may be molded to a hearing protector component or a pressure-sensitive adhesive component for ease of mold removal and/or lower costs of production. In still another embodiment, an in-mold coating is employed in place of a mold release agent. This coating may also serve to make the component more slippery, thereby aiding the device to slide by the ear canal.

The foam component may be encapsulated or further coated if desired, or embossed. The foam component may also be crushed to rupture some of the closed cells to allow at least some air flow. Crushing may prevent puckering, or softens the foam to allow ease of compression. It may then be either glued or otherwise affixed to a seal plate or stem.

Figure 3:
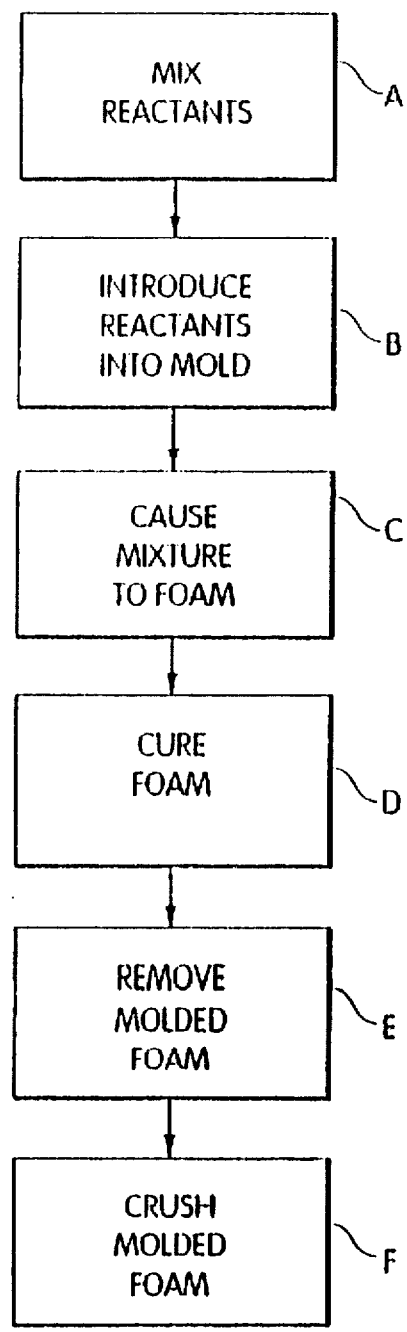
FIG. 3 shows a flow chart of a molding process for making hearing protectors according to the present invention.

As shown in FIG. 3 the reactants are first mixed (A), the mixture is introduced into the mold (B), the mixture is caused to foam (C), and the foam is cured (D), and the molded foam is next removed from the mold (E), and the molded foam is then optionally crushed (F).

The present invention is further illustrated by the following non-limiting examples.

TABLE 1

Formulation and Physical Properties for Standard Size Dynamically Stiff Ear Muff Cushion

| Ingredients | 1 | 2 | 3 | 4 | 5 | 6 | 7 | 8 | 9 | 10 | 11 | 12 | 13 |
|---|---|---|---|---|---|---|---|---|---|---|---|---|---|
| LHT-240 | 56.00 | 56.00 | 56.00 | 56.00 | 56.00 | 56.00 | 56.00 | 56.00 | 56.00 | | 34.00 | 34.00 | 56.00 |
| PPG-425 | 12.00 | 12.00 | 12.00 | 12.00 | 12.00 | 12.00 | 12.00 | 12.00 | 12.90 | | 12.00 | 12.00 | 12.00 |
| LG-56 | 12.00 | 12.00 | 12.00 | 12.00 | 12.00 | 12.00 | 12.00 | 12.00 | 12.00 | | 34.00 | 34.00 | 12.00 |
| Niax 11-34 | | | | | | | | | | 100.00 | | | |
| Y-4347 | 3.60 | 3.60 | 3.60 | 3.60 | 3.60 | 3.60 | 3.60 | 3.60 | 3.60 | 1.20 | 3.60 | 3.60 | 3.60 |
| L-45 | 3.60 | 3.60 | 3.60 | 3.60 | 3.60 | 3.60 | 3.60 | 3.60 | 3.60 | 3.60 | 3.60 | 3.60 | 3.60 |
| 1,4 Butanediol | 1.50 | 1.50 | 1.50 | 1.50 | 1.50 | 1.50 | 1.50 | 1.50 | 1.50 | | 1.50 | 1.50 | 1.50 |
| DE83R | 18.60 | 18.60 | 18.60 | 18.60 | 18.60 | 18.60 | | | | | | | |
| Antimony Oxide | 6.20 | 6.20 | 6.20 | 6.20 | 6.20 | 6.20 | | | | | | | |
| Aluminum Trihydrate | 40.00 | 40.00 | 40.00 | 40.00 | 40.00 | 40.00 | | | | | | | |
| Water | 0.79 | 0.79 | 0.79 | 0.79 | 0.79 | | 0.79 | 0.81 | 1.10 | 1.10 | 0.73 | 0.73 | |
| Methylene Chloride | 9.00 | 9.00 | 9.00 | 9.00 | 9.00 | 9.00 | | | | | 9.00 | 9.00 | |
| UCAR 154 | | | | | | 1.98 | | | | | | | 2.75 |
| Tinuvin | 0.60 | 0.60 | 0.60 | 0.60 | 0.60 | 0.60 | 0.60 | 0.60 | 0.60 | | 0.60 | 0.60 | 0.60 |
| T-12 | 0.10 | 0.10 | 0.10 | 0.10 | 0.10 | 0.10 | 0.10 | 0.10 | 0.10 | 0.10 | 0.10 | 0.10 | 0.20 |
| BL-11 | | 0.10 | 0.10 | 0.10 | 0.10 | 0.10 | 0.10 | 0.10 | 0.10 | 0.04 | 0.10 | 0.10 | 0.10 |
| PPG-566 Green | 0.90 | 0.90 | 0.90 | 0.90 | 0.90 | 0.90 | 0.15 | 0.15 | 0.15 | | 0.15 | 0.15 | |
| 83PC03 Brown | | | | | | | | | | 0.25 | | | |
| 27A14Red | | | | | | | | | | | | | 0.01 |
| Isonate 143L | 47.25 | 46.17 | 45.07 | 43.97 | 50.57 | 47.25 | 47.25 | 47.25 | 47.25 | 26.86 | 39.24 | 43.26 | 47.49 |
| Ratio | 3.49 | 3.57 | 3.66 | 3.75 | 3.26 | 3.51 | 1.91 | 1.91 | 1.92 | 3.96 | 2.53 | 2.29 | 1.94 |
| Index | 75.93 | 74.17 | 72.40 | 70.63 | 81.24 | 75.93 | 77.00 | 75.80 | 70.70 | 100.00 | 77.00 | 85.00 | 70.70 |
| Physical Properties | | | | | | | | | | | | | |
| Height (inches) | 0.669 | 0.662 | 0.654 | 0.662 | 0.701 | 0.651 | 0.673 | 0.662 | 0.655 | 0.656 | 0.654 | 0.662 | 0.660 |
| Density (PCF) | 12.6 | 12.3 | 12.9 | 13.1 | 10.8 | 12.3 | 9.2 | 8.7 | 7.5 | 8.6 | 8.6 | 7.3 | 9.3 |
| Defection 12N (inches) | 0.051 | 0.123 | 0.154 | 0.240 | 0.049 | 0.084 | 0.079 | 0.172 | 0.352 | 0.025 | 0.026 | 0.081 | 0.282 |
| $F_a$ (lbs/inch) | | 82.7 | 18.3 | 11.7 | 57.7 | 53.5 | 35.6 | 16.4 | | 108.5 | 12.5 | 34.9 | 10.0 |
| Insertion Loss: NRR (dB) | | | | | | | | | | | | | |
| Model 1000 | 24.9 | 25.0 | 25.1 | 24.8 | 25.1 | 24.3 | 24.1 | 24.5 | 23.6 | 17.2 | 22.1 | 23.1 | |
| Model 2000 | 27.3 | 27.0 | 27.0 | 27.6 | 26.2 | | | | | 22.7 | 25.5 | | |
| Model 3000 | 27.7 | 27.7 | 27.8 | 28.9 | 26.2 | 27.7 | 26.3 | 26.9 | | 24.4 | 27.1 | | 29.5 |
| Transmissibility | | | | | | | | | | | | | |
| Fn(Hz) | 300 | 160 | 132 | 132 | 356 | 200 | 212 | 180 | 132 | 60 | 60 | 112 | 156 |
| A or $L_t$ (dB) | 4.3 | 30 | 3.1 | 2.8 | 6.2 | 3.8 | 4.1 | 3.7 | 3.5 | 13.9 | 5.7 | 3.8 | 3.1 |
| K* (lbs/inch) | 9187 | 2613 | 1778 | 1779 | 12936 | 4083 | 4588 | 3307 | 1779 | 367 | 367 | 1280 | 2484 |
| η | 0.77 | 1.00 | 0.98 | 1.05 | 0.56 | 0.85 | 0.80 | 0.86 | 0.90 | 0.21 | 0.61 | 0.85 | 0.98 |
| Cushion Number | 82A2 | 96A4 | 94B2 | 95C2 | 95D3 | 98A7 | 3B3 | 3C2 | 5A1 | 8B1 | 12C3 | 13A3 | 15A2 |

| Ingredients | 14 | 15 | 16 | 17 | 18 | 19 | 20 | 21 |
|---|---|---|---|---|---|---|---|---|
| LHT-240 | 56.00 | 56.00 | 56.00 | 56.00 | 56.00 | 56.00 | 56.00 | |
| PPG-425 | 12.00 | 12.00 | 12.00 | 12.00 | 12.00 | 12.00 | 12.00 | |
| LG-56 | 12.00 | 12.00 | 12.00 | 12.00 | 12.00 | 12.00 | 12 00 | |
| Niax 11-34 | | | | | | | | 100.00 |
| Y-4347 | 3.60 | 3.60 | 3.60 | 3.60 | 3.60 | 3.60 | 3.60 | 3.60 |
| L-45 | 3.60 | 3.60 | 3.60 | 3.60 | 3.60 | 3.60 | 3.60 | 3.60 |
| 1,4-Butanediol | 1.50 | 1.50 | 1.50 | 1.50 | 1.50 | 1.50 | 1.50 | 1.50 |
| DE83R | 18.60 | | 18.60 | 18.60 | 18.60 | 18.60 | 18.60 | |
| Antimony Oxide | 6.20 | | 6.20 | 6.20 | 6.20 | 6.20 | 6.20 | |
| Aluminum Trihydrate | 40.00 | | 40.00 | 40.00 | 40.00 | 40.00 | 40.00 | |
| Water | 0.79 | | 0.79 | 0.79 | 0.79 | 0.79 | 0.79 | 1.10 |
| Methylene Chloride | 9.00 | | 9.00 | 9.00 | 9.00 | 9.00 | 9.00 | |
| UCAR 154 | | 2.75 | | | | | | |
| Tinuvin | 0.60 | 0.60 | 0.60 | 0.60 | 0.60 | 0.60 | 0.60 | |
| T-12 | 0.10 | 0.20 | 0.10 | 0.10 | 0.10 | 0.10 | 0.10 | 0.10 |
| BL-11 | 0.10 | 0.10 | | 0.10 | 0.10 | 0.10 | 0.10 | 0.10 |
| PPG-566 Green | 0.90 | | 0.90 | 0.90 | 0.90 | 0.90 | 0.90 | |
| 83PC03 Brown | | | | | | | | 0.15 |
| 27A14Red | | 0.01 | | | | | | |
| Isonate 143L | 45.07 | 47.49 | 47.25 | 46.17 | 45.07 | 43.97 | 50.57 | 31.64 |
| Ratio | 3.66 | 1.94 | 3.49 | 3.57 | 3.66 | 3.75 | 3.26 | 3.48 |
| Index | 72.40 | 70.70 | 75.93 | 74.17 | 72.40 | 70.63 | 81.24 | 100.00 |

TABLE 1-continued

Formulation and Physical Properties for Standard Size Dynamically Stiff Ear Muff Cushion

| Physical Properties | | | | | | | | |
|---|---|---|---|---|---|---|---|---|
| Height (inches) | 0.491 | 0.501 | 0.411 | 0.412 | 0.411 | 0.405 | 0.418 | 0.404 |
| Density (PCF) | 13.1 | 8.5 | 12.9 | 14.8 | 15.0 | 15. | 13.4 | 11.7 |
| Defection 12N (inches) | 0.096 | 0.202 | 0.036 | 0.034 | 0.051 | 0.063 | 0.017 | 0.019 |
| $K_a$ (lbs/inch) | 29.4 | 14.30 | 79.0 | 82.7 | 55.2 | 34.0 | 169.3 | 151.1 |
| Insertion Loss NRR (dB) | | | | | | | | |
| Model 1000 | 25.3 | 24.6 | 26.2 | 25.8 | 25.3 | 26.4 | 26.4 | 20.7 |
| Model 2000 | 27.7 | 28.0 | 28.5 | 27.8 | 28.3 | 28.3 | 28.3 | 24.6 |
| Model 3000 | 29.1 | 29.7 | 28.7 | 29.5 | 29.5 | 29.3 | 28.8 | |
| Transmissibility | | | | | | | | |
| Fn(Hz) | 164 | 200 | 336 | 324 | 256 | 208 | 504 | 84 |
| A or $L_\tau$ (dB) | 2.8 | 3.7 | 4.4 | 4.0 | 3.0 | 3.0 | 8.0 | 11.8 |
| K (lbs/inch) | 2745 | 4083 | 11524 | 10715 | 6689 | 4416 | 25928 | 720 |
| η | 1.05 | 0.86 | 0.76 | 0.81 | 1.00 | 1.00 | 0.43 | 0.27 |
| Cushion Number | 10A3 | 15B5 | 89A6 | 96B1 | 96C2 | 96D2 | 96A2 | 6C2 |

EXAMPLE 1

Polyol, catalyst, filler, plasticizer, antifoam agent, surfactant and internal mold release agents were premixed at room temperature (see Table 1 for specific compositions; the owners/sources of the trademarks/products are listed in Table 2). The material was introduced into a preheated earmuff cushion mold at a temperature (about 50° C.) sufficient to cause foaming as part of a two stream introduction of materials (mix/meter machine). The isocyanate was added as the second stream. The earmuff cushions were then removed from the mold as quickly as possible to prevent puckering and crushed in order to open some of the as-formed closed cells. The cushions were bonded to the seal plate using conventional pressure sensitive adhesive. The liners were inserted, and the headband attached, all in conventional fashion. Testing was performed with the earmuffs to demonstrate the increased attenuation as discussed below.

EXAMPLES 2-21

Polyol, catalyst, filler, plasticizer, antifoam agent, surfactant and internal mold release agents were premixed and degassed at room temperature. The isocyanate was added thereto, and the mixture degassed once again. The material was poured into an earmuff cushion mold at a temperature sufficient to cause foaming (e.g., about 50° C.). The formed earmuff cushions were then removed from the mold and processed as set forth in Example 1 above.

TABLE 2

| Materials Source List | | | |
|---|---|---|---|
| Brand name | Source List | Function | Equivalent Weight |
| Arcol LHT 240 | Arco Chemical | Low MW Triol | 234 |
| Arcol PPG 425 | Arco Chemical | Low MW Diol | 210 |
| Arcol LG 56 | Arco Chemical | Medium MW Triol | 1000 |
| Arcol 11-34 | Arco Chemical | High MW Triol | 1580 |
| Y-4347 | Union Carbide | Cell Stabilizer | — |
| L-45 (350) | Union Carbide | Cell Regulator | — |
| 1,4-Butanediol | GAF | Chain Extender | 45 |
| DE 83R | Great Lakes Chem | Fire Retardant | — |
| Antimony Oxide | Amspec Chemical | Fire Retardant | — |
| Aluminum Tri-hydrate | Solem Industries | Fire Retardant | — |
| Methylene Chloride | Dow Chemical | Blowing Agent | — |
| UCAR 154 | Union Carbide | Cell Stabilizer | 22.5 |
| Tinuvin 765 | Ciba Geigy | HALS | — |
| Dabco T-12 | Air Products | Catalyst | — |
| Dabco BL-11 | Air Products | Catalyst | — |
| PPG-556 | Dayglo | Colorant | — |
| Stantone 83PC03 | Harwick Chemical | Colorant | — |
| Stantone 27A14 | Harwick Chemical | Colorant | — |
| Isonate 143L | Dow Chemical | Isocyanate | 143 |
| HYPOL 2000 | Hampshire Chemical | PEO Polyurethane prepolymer | — |
| Pluronic F-68 | BASF | Surfactant | — |
| Pluronic 25R2 | BASF | Surfactant | — |
| Superfine/Superfloss | Barretts Minerals | Filler | — |
| Sun Yellow YFD-1123 | Sun Chemical | Colorant | — |

TABLE 3

How to Calculate NRR

| OCTAVE BAND FREQUENCY (Hz) | 125 | 250 | 500 | 1000 | 2000 | 4000 | 8000 |
|---|---|---|---|---|---|---|---|
| 1. Hypothetical noise spectrum OB sound levels (pink noise) | 100.0 | 100.0 | 100.0 | 100.0 | 100.0 | 100.0 | 100.0 |
| (level assumed is not significant) | | | | | | | |
| 2. C-weighted OB sound levels unprotected ear | 99.8 | 100.0 | 100.0 | 100.0 | 99.8 | 99.2 | 97.0 |
| 3. Overall C-weighted sound level (logarithmic sum of the seven OB sound levels in step 2) | 108.0 dBC | | | | | | |
| 4. A-Weighted OB sound levels unprotected ear | 83.9 | 91.4 | 96.8 | 100.0 | 101.2 | 101.0 | 98.9 |
| 5. E-A-R ® Plug mean attenuation | 29.6 | 31.3 | 34.1 | 34.0 | 35.5 | 41.4* | 39.6** |
| 6. E-A-R ® Plug standard deviations x2 | 6.4 | 6.6 | 4.2 | 4.6 | 5.4 | 3.9* | 4.6* |
| 7. Protected A-weighted OB sound levels (Step 4 − Step 5 + Step 6) | 60.7 | 66.7 | 66.9 | 70.6 | 71.1 | 63.5 | 64.1 |

8. Overall A-weighted sound level under the protector (effective exposure)-76.0 dBA (logarithmic sum of the seven OB sound levels in step 7)
9. NRR = Step 3 − Step 8 − 3 dB
NRR = 108.0 − 76.0 − 3 = 29 dB OB: Octave band (This is a correction (safety) factor to protect against overestimating the device's noise reduction because of possible variations in the spectra of actual industrial noises.
*Numerical average of the 3000 $H_z$ and 4000 $H_z$ data.
**Numerical average of the 6000 $H_z$ and 8000 $H_z$ data

EXAMPLE 22

Figure 22:
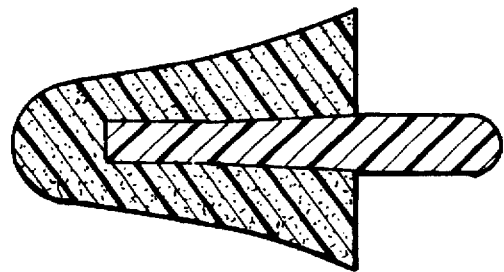
FIG. 22 is a sectional view of an alternative embodiment of an earplug having a stiffening member according to the present invention.

A semi-aural pod similar to that shown in FIG. 22 was formed by mixing the polyol formulation according to the Table below with isocyanate (HYPOL 2000) in a 1:1 ratio in a mix/meter machine, and introducing the mixture into molds having cavities of the desired shape which were oversize by 12% in each dimension to allow for shrinkage. Mold tops containing stems were placed on the molds such that the final foam would be placed forward of the stem and the molds clamped shut. After seven minutes, the molds were opened, and pods were dried. Average physical properties of the pods are listed in the Table below:

| Ingredients | Part by Weight |
|---|---|
| UCAR 154 | 2500 |
| 20% Pluronic F-68 | 138 |
| Pluronic 25R2 | 3.3 |
| Superfine/Superfloss | 164 |
| Sun Yellow YFD 1123 | 33 |
| Water | 421 |
| Physical Properties, units | |
| Weight, g | 0.445 |
| Total length, inches (mm) | 1.252(31.80) |
| Foam length, inches (mm) | 0.818(20.78) |
| Stem Length | 1.009(25.63) |
| Outer Stem Diameter | 0.180(4.57) |
| Inner Stem Diameter | 0.125(3.18) |
| Foam Weight, g | 0.331 |
| Maximum Foam Diameter, inch (mm) | 0.635(16.13) |
| Foam Diameter 0.500 Inches from Tip, inches (mm) | 0.429(10.90) |
| Foam Diameter 0.600 inches from Tip, inches (mm) | 0.471(11.96) |
| Foam Forward of Stem, inches | 0.243(6.17) |

EXAMPLE 24

Another semi-aural pod for testing were formed by mixing the 32.94 parts by weight of the polyol formulation according to the Table below with 16.51 parts by weight isocyanate (Isonate 143L), thus achieving a ratio of 1.995. The mixture was poured onto molds (preheated to 50° C.) having cavities of the desired shape. Mold tops containing stems were placed on the molds such that the final foam would be placed forward of the stem and the molds clamped shut. After ten minutes, the molds were opened, and the foam pods were removed. The pods were post-cured at 55° C. for two hours. Physical properties of the pods are listed in the Table below:

| Ingredients | Part by Weight |
|---|---|
| Arcol LHT 240 | 56.0 |
| Arcol PPG 425 | 12.0 |
| Arcol LG 56 | 12.0 |
| 1,4-Butanediol | 1.5 |
| Tinuvin 765 | 0.60 |
| Dabco T-12 | 0.100 |
| Dabco BL-11 | 0.050 |
| Y 4347 | 5.568 |
| L-45 | 2.225 |
| Water | 0.900 |
| Sun Yellow YFD 1123 | 1.385 |
| Physical Properties, units | |
| Weight of Pod, g | 0.608 |
| Average Weight of Stem, g | 0.115 |
| Weight of foam, g | 0.493 |
| Volume of Foam, in$^3$ (mm$^3$) | 0.1779(2.91) |
| Density of foam, lbs/ft$^3$ (g/mm$^3$) | 11.15(0.0395) |

Testing

The following tests were performed on the foams making up the foam components of the present invention. Because it may be difficult to test foam pods and earplugs for dynamic spring constant, especially if they have stems, the majority of tests were run on foams tested as earmuff cushions according to the procedure described in U.S. Pat. No. 5,420,381 to Gardner and Simon. When tested according to these methods, preferred hearing protector components have a static spring constant of up to about 60 pounds per inch, and the most preferred hearing protector components have a static spring constant of up to about 30 pounds per inch. The preferred hearing protector components also have a dynamic spring constant of at least about 300 pounds per inch, and most preferably up to about 1000 pounds per inch.

1. Attenuation Testing and Insertion Loss Testing

Attenuation testing and Insertion Loss (IL) testing are conducted in accordance with ASA STD 1-1975 (ANSI S3.19), "Method for the Measurement of Real-Ear Protection of Hearing Protectors and Physical Attenuation of Earmuffs". The artificial flesh supplied for the physical method did not meet the Shore 00 durometer requirement of 20±5 stated in the above procedure. Therefore, an artificial flesh made of silicone rubber was made having a measured Shore durometer of 20, being 0.385 inch thick and having a Knowles Electronic pinna over the microphone center. The pinna was obtained from Industrial Research Products, Inc., a Knowles Company.

Insertion Loss testing employs an artificial test fixture (ATF) having artificial flesh yielding insertion loss results for earmuffs which are similar to those attained using real ear testing at threshold (REAT). When using the ATF it should be remembered that attenuation results for better earmuffs are usually bone conduction limited to 35 dB± about 2 at 2000 Hz.

The EPA has selected the NRR as a measure of hearing protector's noise reducing capabilities. The range of noise reduction ratings for existing hearing protectors is approximately 0 to 30.

When estimating NRR from IL test results, we used 10 dB and 20 dB for minimum 125 Hz insertion loss values for the E-A-R® Model 1000 and Model 3000 earmuffs respectively. These values were only required for the normal earmuffs as earmuffs utilizing dynamically stiff cushion yield higher values. Standard deviations of 3.0 are employed in calculating estimated NRRs. This value is typical of measured values.

Figure 4:
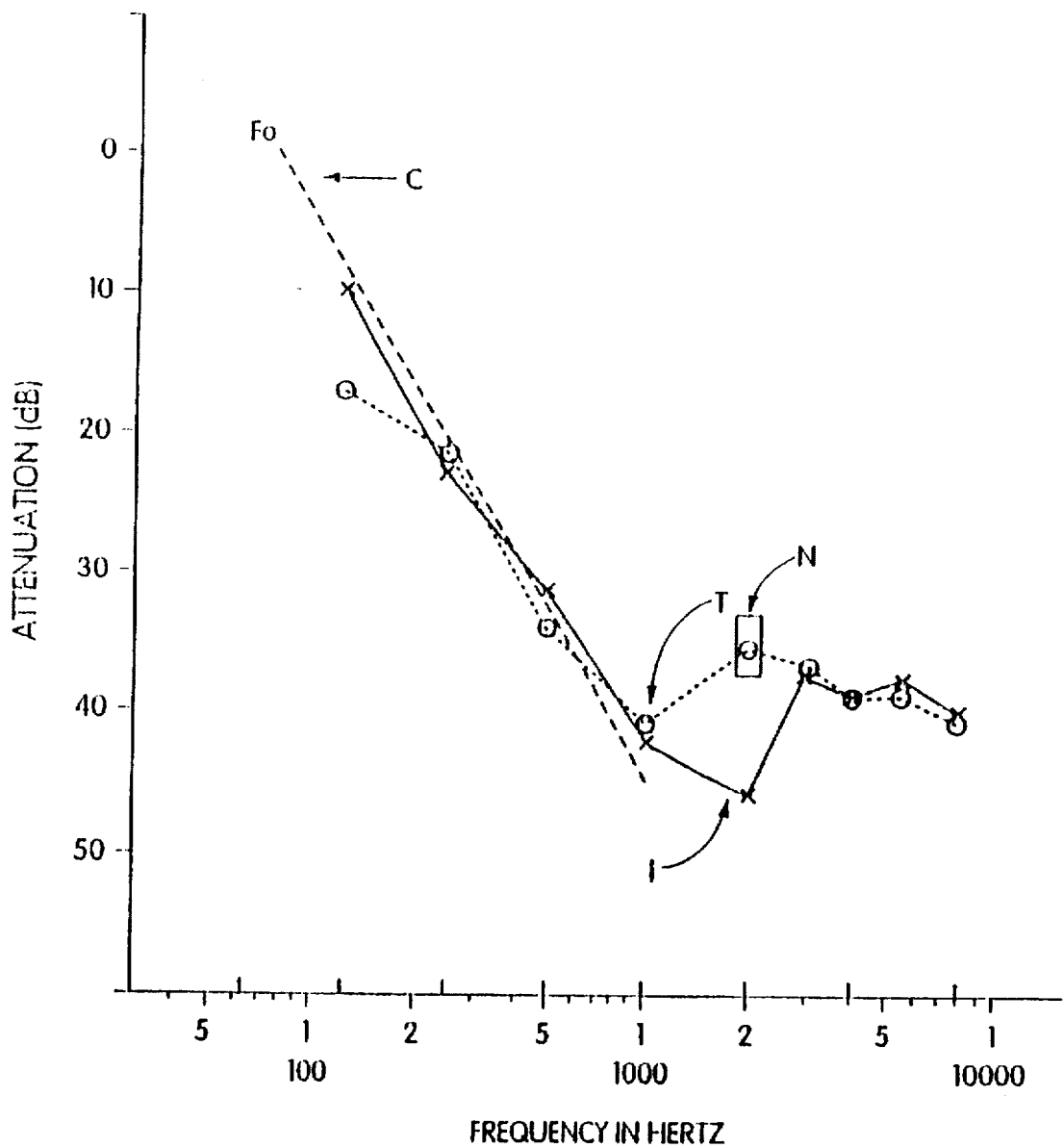
FIGS. 4 and 5 show comparisons of REAT, IL, and calculated attenuation for earmuffs.
Figure 5:
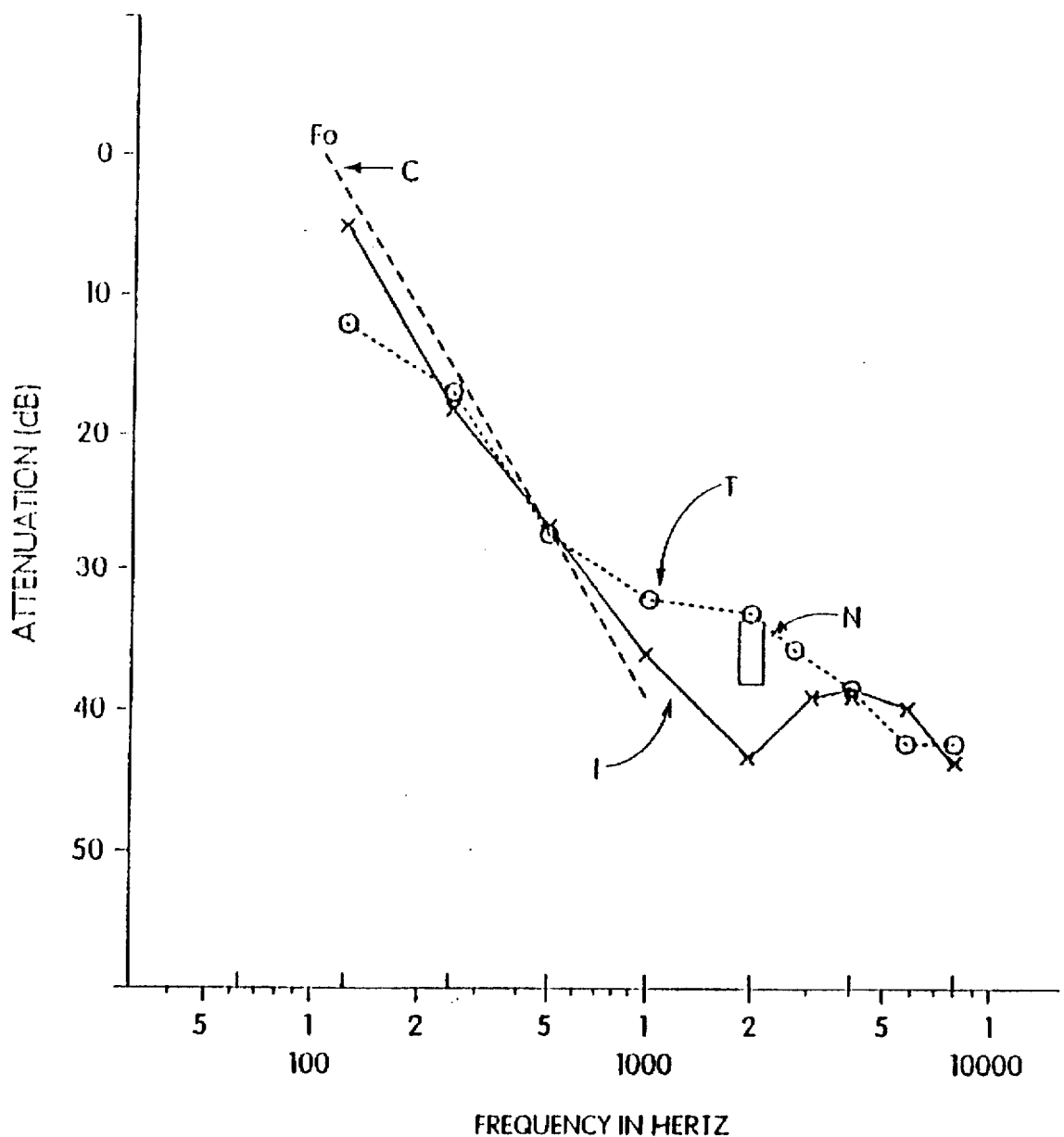

Insertion Loss measurements are only used in lieu of REAT measurements. FIGS. 4 and 5 show comparisons of REAT, IL and calculated attenuation for conventional Model 3000 and Model 1000 Earmuffs respectively. These FIGURES are used as a basis for using IL in lieu of REAT for the purpose of evaluating dynamically stiff cushions.

In FIGS. 4 and 5, C is the calculated value, T is the result of 10 subject tests, N is the nominal limit due to bone conduction and I is the insertion loss. The calculated attenuation obtained by determining the frequency at 0 dB Attenuation ($F_0$) using the expression:

$$F_o^2 = A^2/VM \times 35460$$

Where:

A=Area bounded by the cushion outer edge (cm$^2$)

V=Volume (cm$^3$)

M=Mass (g)

In FIG. 5 the increase in attenuation with frequency is applied using a 12 dB/octave.

2. Static Deflection Testing

Figure 6:
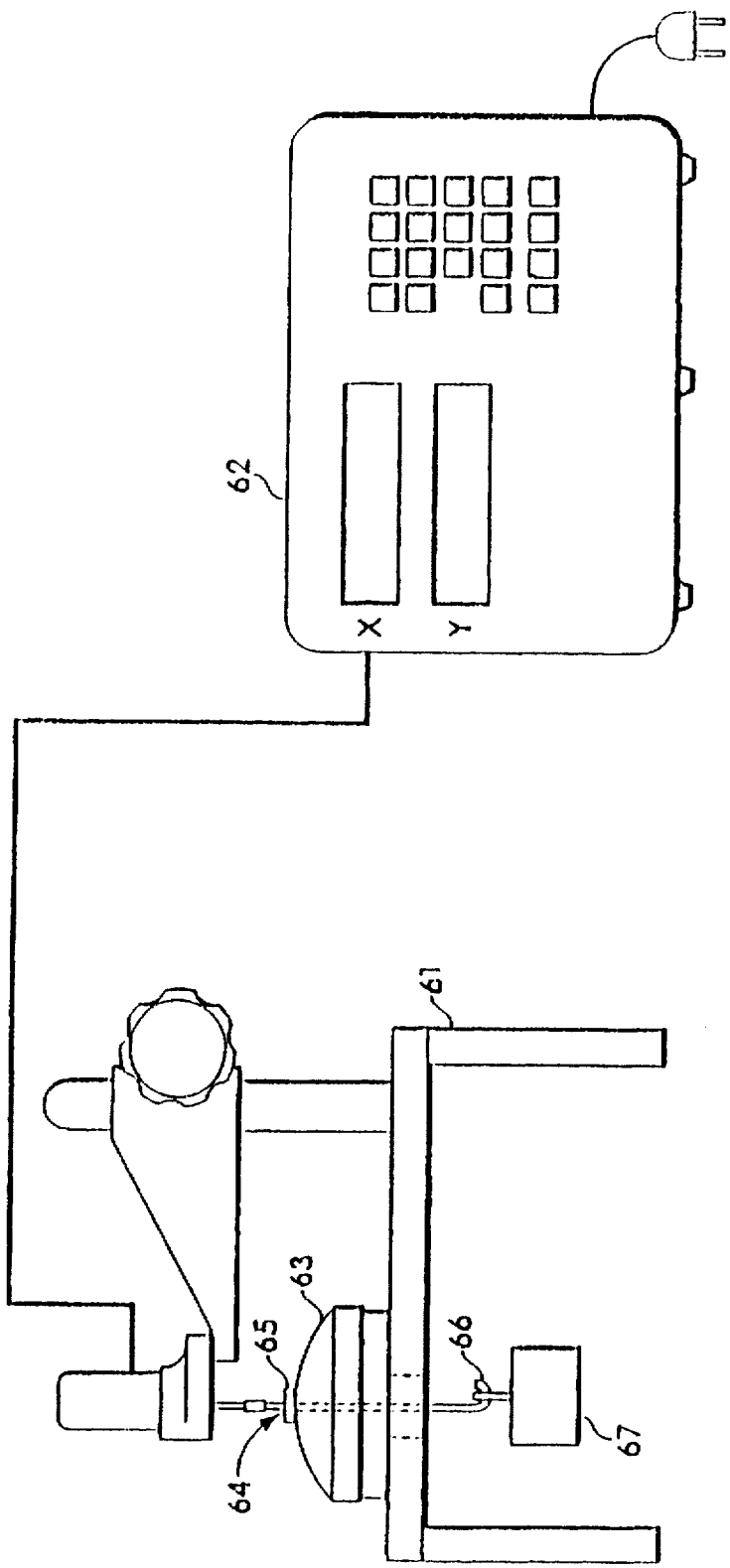
FIG. 6 shows a static deflection measuring apparatus.

Static deflection is measured on an apparatus shown in FIG. 6. The apparatus consists of a platform 61 with an attached adjustable electronic thickness gauge 62. The earmuff cup 63 has a hole 64 at the center of the top. At the top of the hole is a flat plate 65 with attached hook 66 which protrudes through a hole in the platform so as to receive a 12.5 Newton weight 67.

The earmuff cup with cushion in position is placed under the electronic thickness gauge and the gauge is zeroed. Simultaneously with adding a 12.5 Newton weight to the hook a stopwatch is started. After 10 minutes the deflection is read from the electronic thickness gauge and recorded.

In these experiments the earmuff cup employed is from an E-A-R® Model 1000 Earmuff. The plate cup and hook weighed 90 grams exclusive of the cushion.

3. Transmissibility Testing

Figure 7:
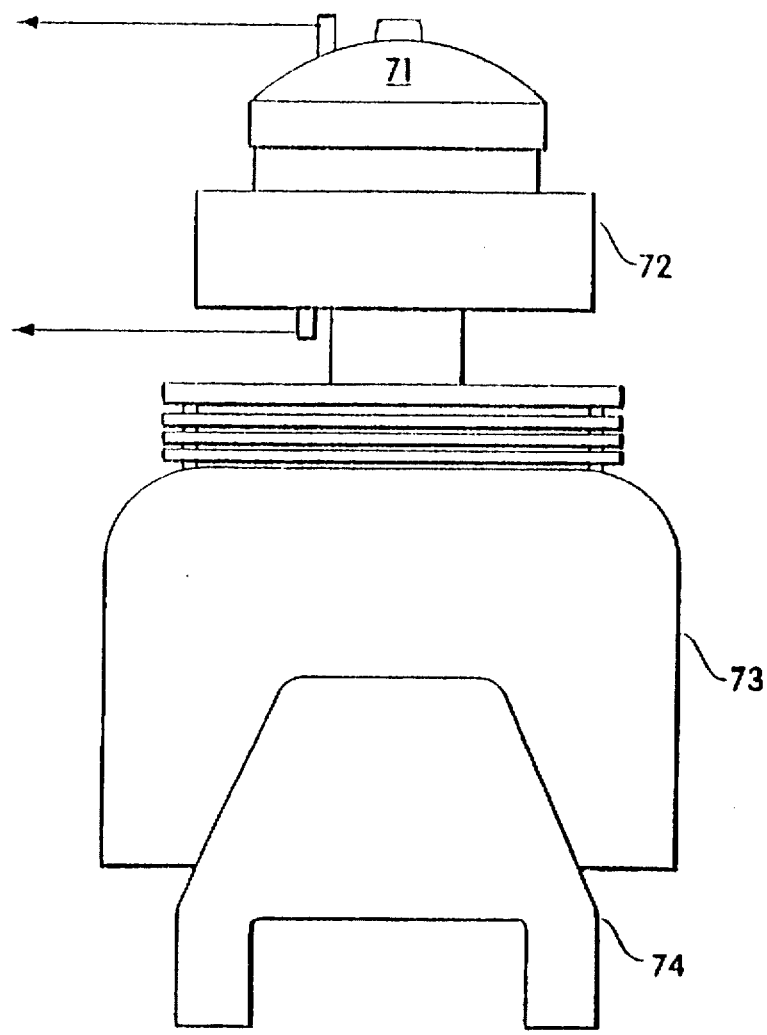
FIG. 7 shows a transmissibility measuring apparatus.
Figure 8:
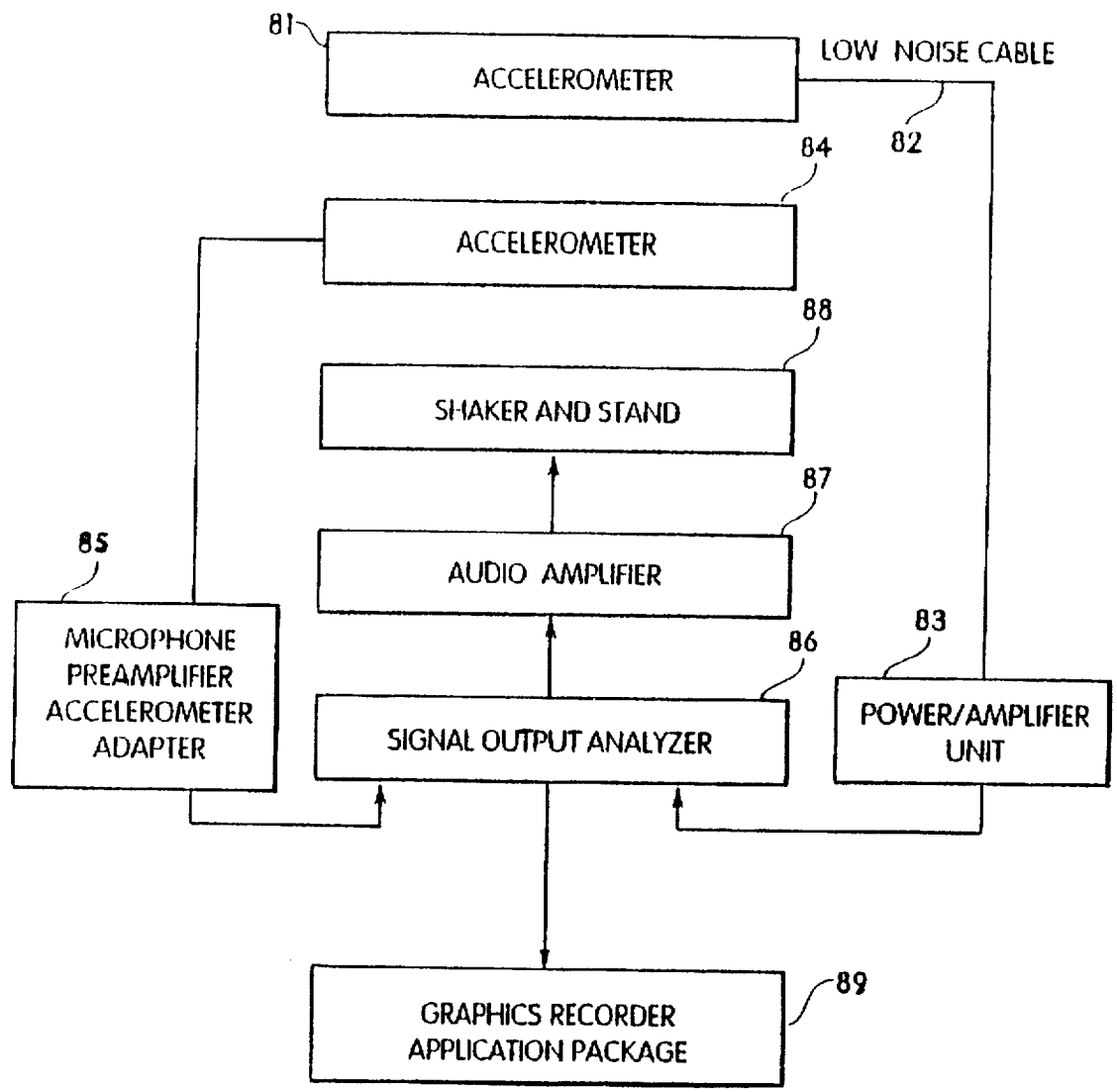
FIG. 8 shows a transmissibility measuring system.

Transmissibility measurements are taken using the fixture shown in FIG. 7 and the equipment shown in the block diagram in FIG. 8.

For this work it was shown that adding weight to the cup to a total weight of 1.00 pound (454 grams) using barium sulfate filled epoxy resin was necessary to ensure adequate contact of the cushion to the platform. This total weight of 1.00 pound was employed during all tests.

Also, adequate stiffness of all connections and of the platform itself must be assured so as to give a straight line output free of secondary resonances to at least 1000 Hz. The platform used in this work was 5.0 inch (12.7 cm) in diameter, and 1.50 inch (3.81 cm) thick brass.

The test procedure used (with reference to FIGS. 7 and 8) was as follows: Place the earmuff cup 71 with attached cushion and mass on top of the shaker platform 72. Shaker 73 and stand 74 support the platform. With an input level of 0.2 G (acceleration of gravity, 32 feet/second/second) obtain a transmissibility curve having the cursor at the natural frequency. Read and record the natural frequency (Fn) in Hz and the amplification (A) in dB. In FIG. 8 the accelerometer (81) is connected through the low noise cable (82) to the power/amplifier unit (83). The power/amplifier unit is connected to the signal output analyzer (86) which is connected to the audio amplifier (87) and shaker and stand (88). The accelerometer (84) is connected to the microphone preamplifier and accelerometer adapter (85) which is also connected to the signal output analyzer. The signal output analyzer is connected to the graphics recorder application package (89). The components are all commercially available, e.g., the accelerometer (81) is a PCB 303A02; the low noise cable is PCB Model PCB 002C05; the power/amplifier (83) is PCB model 40D06; the low noise cable (82) can also be a PCB 003810; the signal output analyzer (86) is a Bruel and Kjaer Model 30282FFT; the audio amplifier (87) a Proton model D540; the shaker and stand (88) are MB Electronics Model ER1500; the accelerometer (84) is Bruel and Kjaer Model '4693; the microphone preamplifier and accelerometer adapter (85) are Bruel and Kjaer Model 2619 and W/JJ2615 respectively; the graphics recorder (89) and application package are Bruel and Kjaer Model 2313 and W/827006 respectively. The cables are all standard commercially available low noise cables as described above.

Figure 9:
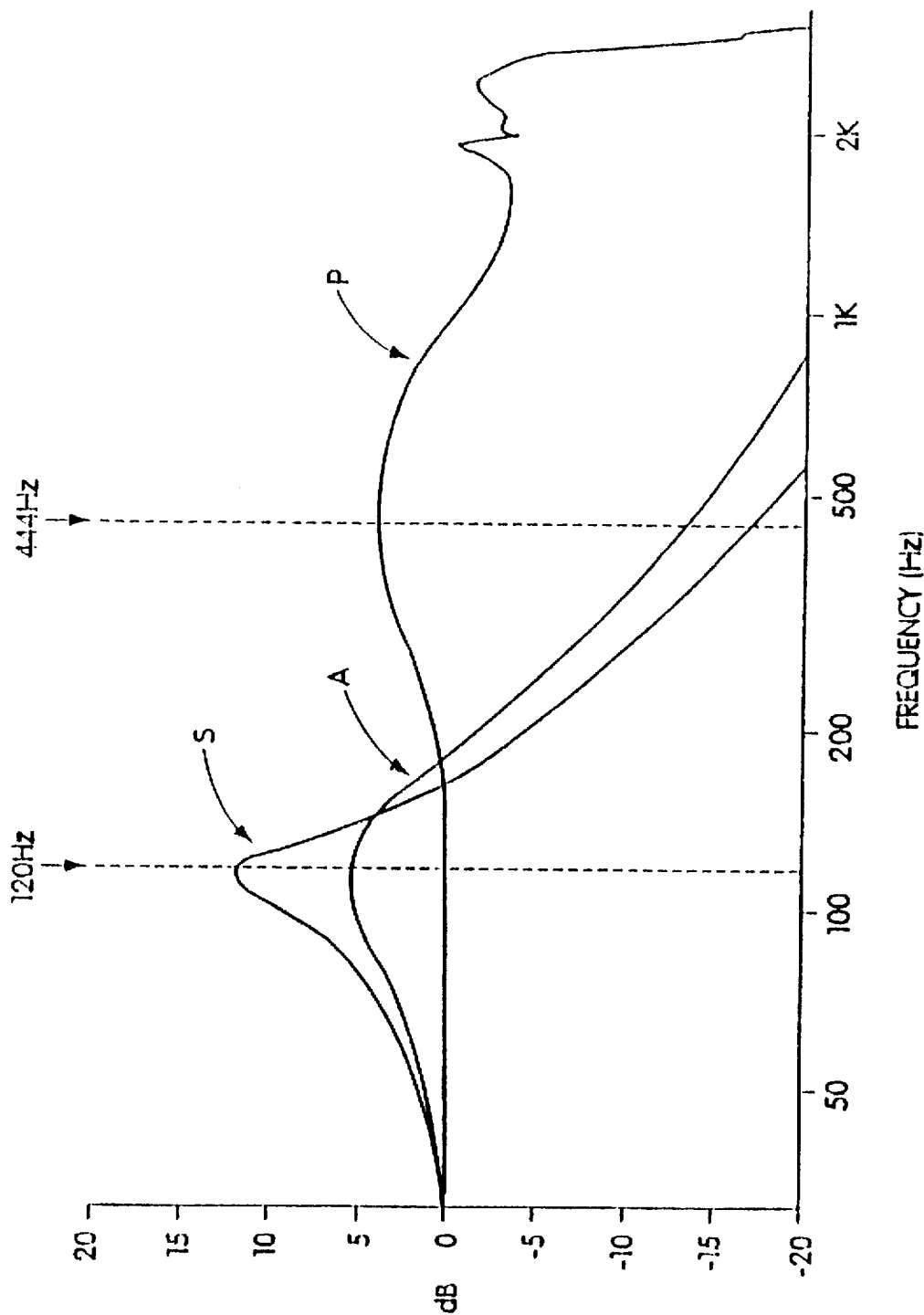
FIG. 9 shows transmissibility tracings for an earmuff.

FIG. 9 shows transmissibility tracings for the E-A-R® Muff Model 1000 with 3 different cushions according to the above-described procedure. In FIG. 9 the standard is shown by curve S, a HYPOL® urethane/acrylic material is shown by curve A and the polyurethane material of the present invention is shown by curve P. The Fn is directly related to the dynamic complex spring constant (K*) of the cushion and the amplification at resonance (A, sometimes referred to as $L_T$) to the material loss factor. Since the K* and η vary with frequency, the exact weight of 1.00 pound (454 gram) weight must be used to determine these values. K* and η are calculated using the following equations:

$$K^* = ((Fn)^2/3.13) \, W \text{ lbs/inch}$$

Where

W=weight (lbs)

$\eta = 1/((10^{L_T/20})^2 - 1)$

Where $L_T$=A=level of transmissibility at resonance (dB).

4. Earmuff Attenuation

Figure 10:
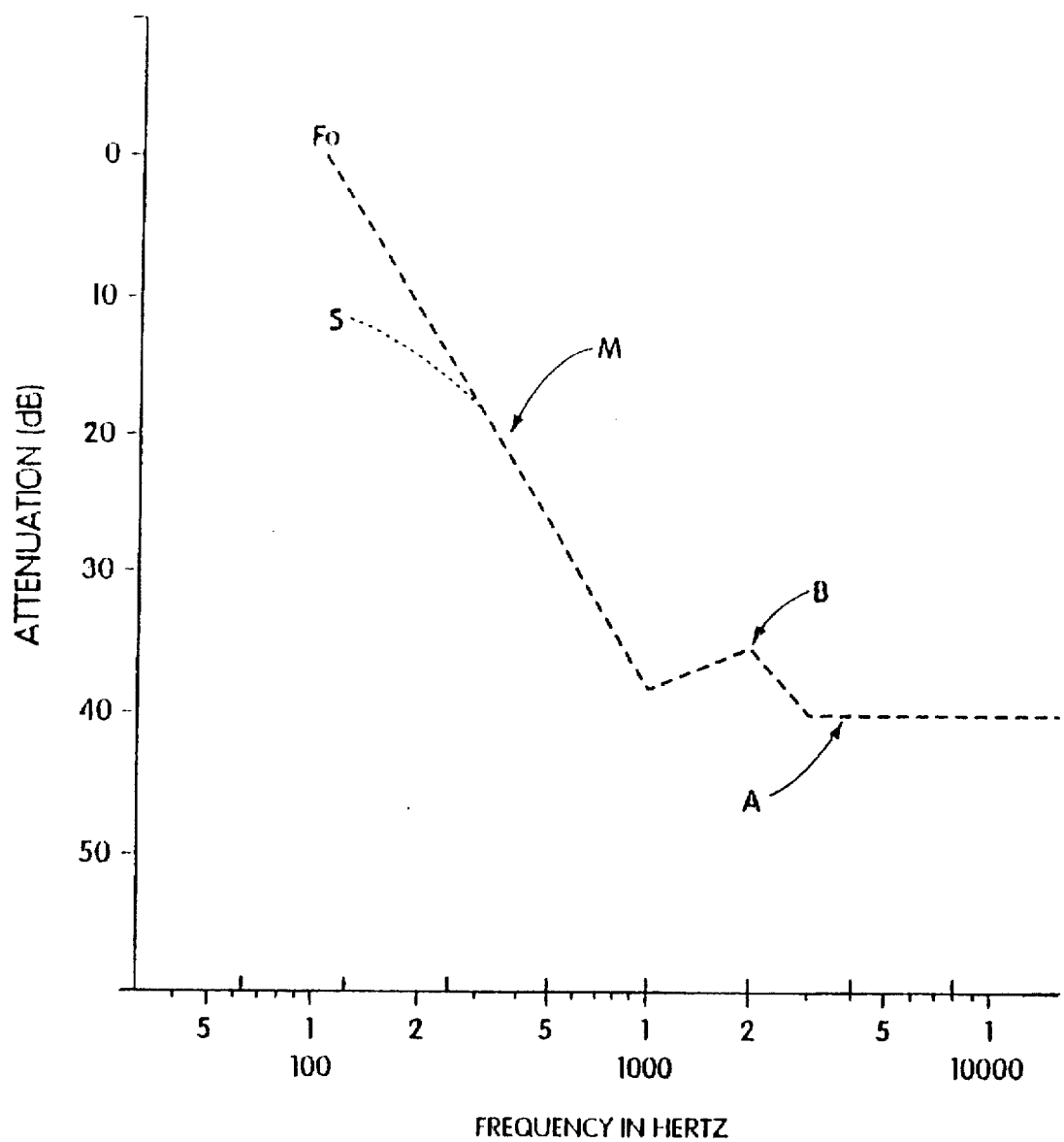
FIG. 10 shows controlling factors for earmuff attenuation.
Figure 11A:
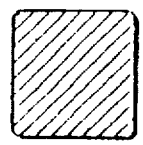
FIGS. 11A–H show shapes of various earmuffs.
Figure 11B:
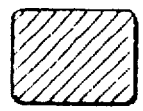
Figure 11C:
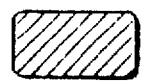
Figure 11D:
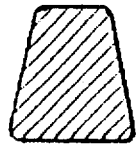
Figure 11E:
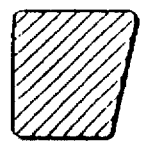
Figure 11F:
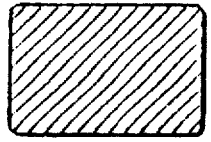
Figure 11G:
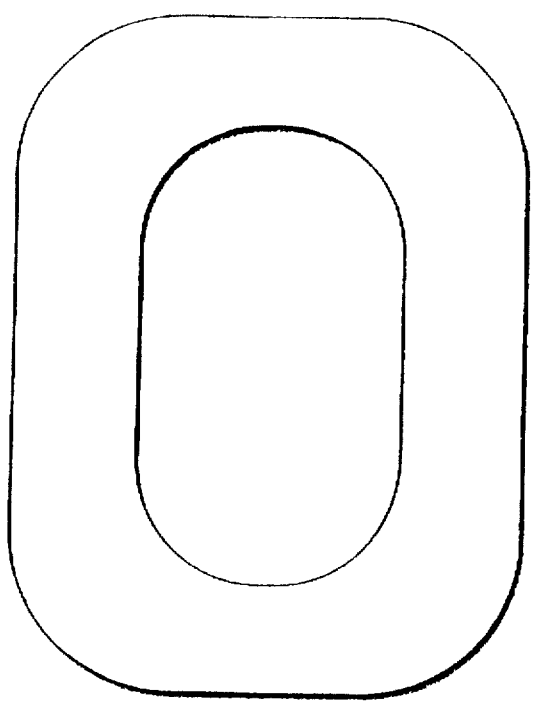
Figure 11H:
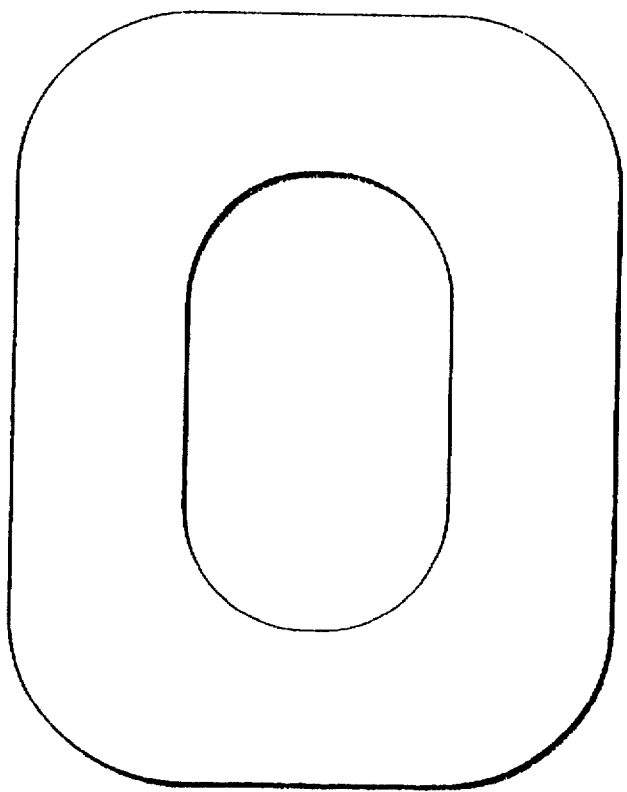

A simplified diagram showing the controlling factors for earmuff attenuation is shown in FIG. 10. Occlusion effect of the cushion/flesh stiffness is shown by curve S, the mass by curve M and the bone conduction by limit by B and the stiffness surface area absorption by A. The low frequency calculations are as follows:

Low Frequency: $F_o = A/2\pi \; PC^2/VM$: $PC^2/(2\pi)^2 = 35460$ $:F_o^2 = A^2/VMX35460$ Where $F_o$=Frequency at 0 dB attenuation A=area bounded by the cushion outer edge V=volume M=mass P=density of air C=speed of sound in air At very low frequencies (normally up to 125 or 250 Hz) the cushion/flesh stiffness controls earmuff attenuation. Additionally, the occlusion effect causes a somewhat higher apparent attenuation at the lower frequencies due to masking by body noise when wearing a hearing protector. Generally, this frequency stiffness controlled attenuation is thought to be limited by the low stiffness of the flesh about the ear. Even the cushion stiffness is limited by the balance between wearer comfort and the ability of the cushion to produce an acoustical seal against the head.

Figure 13:
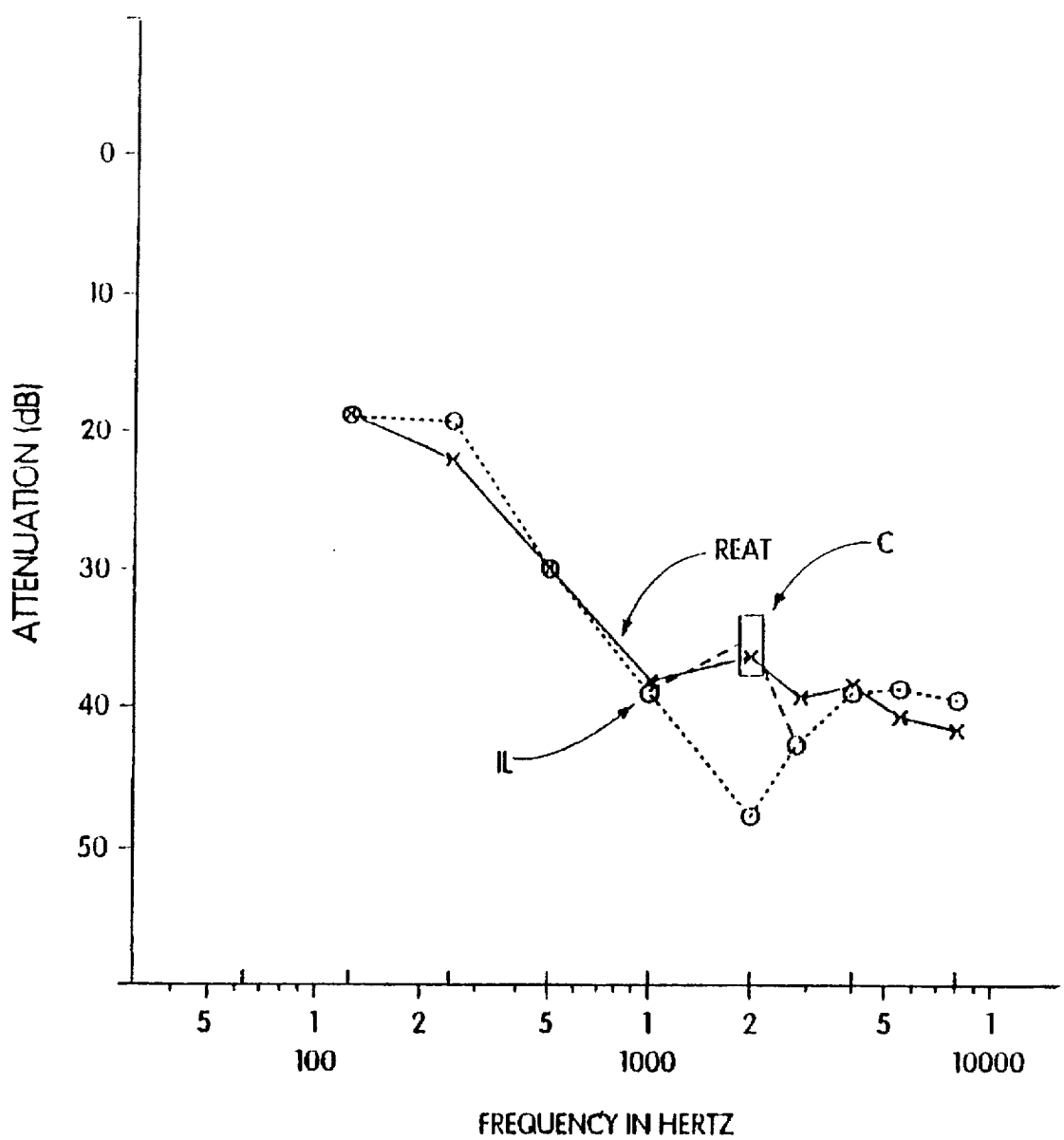
FIG. 13 shows a comparison of REAT to IL values as a function of frequency for earmuffs.

The low frequency attenuation from 125 to 1000 Hz can be predicted by calculating the frequency at 0 dB attenuation using the equations as described for FIGS. 7, 8, or 13 and then extrapolating by drawing a descending line increasing in attenuation by 12 dB per octave up to 1000 Hz. Above 1000 Hz earmuff attenuation is controlled by the surface area of the cup, absorption within the cup, stiffness of the cup and at some frequencies (notably 2000 Hz) by bone conduction. Bone conduction or body conduction is sound reaching the inner ear by other paths besides directly down the ear canal.

Since earmuffs normally have large attenuation values at frequencies above 1000 Hz, these frequencies yield adequate protection and traditionally have presented little or no problems. However, much lower attenuation values are attained at frequencies below 1000 Hz, and therefore increases in attenuation within this frequency range can yield significant increases in protection and in the resultant Noise Reduction Rating (NRR).

5. Noise Reduction Rating (NRR)

The Noise Reduction Rating (NRR), a variant of the NIOSH $R_c$ factor, is the current EPA-proposed single number descriptor. The NRR is fully defined in EPA (1979) *Noise Labeling Requirements for Hearing Protectors*, Federal Register, Vol. 42, No. 190, 40 C.F.R. Part 211, 56139–56147. A sample NRR calculation is shown in Table 3. The key point to consider is that the NRR is subtracted from the measured (unprotected) C-weighted sound level to yield an effective A-weighted sound exposure for the employee. The idea of subtracting a noise reduction factor from a C-weighted sound level to find an A-weighted exposure was first proposed by Botsford in 1973. This "C-A concept" is the important common ingredient in all of the successful single number descriptors proposed in recent years. As can be seen in Table 3, the NRR is the difference between the overall C-weighted sound level of a pink (flat by octaves) noise spectrum and resulting A-weighted noise levels under the protector. The attenuation values used in the calculation are the measured laboratory attenuation values minus two standard deviations. This correction assures that the attenuation values used in the calculation procedure are actually realizable by the majority of employees who conscientiously and correctly wear their protectors. This correction will not account for employee misuse or abuse of the protectors.

6. Earmuff Cushion Shapes and Sizes vs. Insertion Loss

Dynamically stiff polyurethane foam earmuff cushions of Example 1 were made into various shapes shown in FIGS. 11A through 11H. In FIGS. 11A through 11F the following cushions are shown in cross sections: the standard cushion (A); medium cushion (B); thin cushion (C); tapered cushion (D); reversed taper (E); and large (F). The back plates are shown for all cushions except for large (11G) and for large cushions (11H). The hole in the cushions lines up with the hole in the back plate. The upper portion of each cross section as shown is that normally contacting the head.

Insertion Loss was measured for these various shapes. Of the various shapes as measured on the E-A-R® Model 1000 Earmuff several conclusions were drawn:

1. All dynamically stiff cushions are superior to normal Model 1000 cushions with respect to low frequency attenuation and estimated NRR.
2. The Reversed Taper cushions yield the highest low frequency insertion losses and NRR. This cushion is followed by the Thin, Standard and Tapered shapes respectively.
3. The Tapered cushion when inverted so as to give the same area of contact with the head as the Standard cushion gave similar results.
4. Crushing the foam cushion had no significant effect on Insertion Loss.
5. The Reversed Taper, Thin and Large cushions all yielded higher high frequency insertion loss.

Of the various shapes as measured on the E-A-R® Model 3000 earmuff, a somewhat different conclusion may be drawn. All dynamically stiff cushions are superior to normal Model 3000 cushions for low frequency Insertion Loss but many shapes do not result in higher estimated NRRs. The Reverse Taper and Thin cushions are exceptions. The rest of the shapes end up with the ¾ K Hz frequencies controlling the NRR and limiting further increase. Later experiments will utilize an optimized foam liner to further increase high frequency insertion loss.

A total of 14 formulations have been made into earmuff cushions (see Table 1). Five of these formulations, Examples 1 through 5, are a series having high filler (flame retardant) concentrations being from softest to hardest respectively. The remaining formulation have changes as follows:

| Sample Number | Change |
| --- | --- |
| 6, 15, 1 | Water added as part of Latex, UCAR |
| 7, high index | Filler & methylene chloride omitted, low water |
| 8, med index | Filler & methylene chloride omitted, med. water |
| 9, low index | Filler & methylene chloride omitted, high water |
| 21 | High MW Polyol and 100% index |
| 10, 1,4-Butanediol | High MW Polyol and 100% index, drop |
| 11 | Increase conc. of high MW Polyol, decrease low MW Polyol of 3B |
| 12 | Same as 12C but increased index |

| Sample Number | Change |
|---|---|
| 11/12 | No filler or MeCl, water added as UCAR 154, index as 95° C., softest |

Of the above formulations the soft to hard series of five formulations are aimed at producing a cushion in Standard or Thin cross-section which may help to define the upper limit of suitability for hardness i.e. lowest static deflection. Example formulations 21, 10, 11 and 12 are aimed at producing cushions helping to define the lower limit of suitable dynamic stiffness. The remaining formulations are aimed at producing a series of lower density material allowing greater definition of preferred physical characteristics.

Equipment

Although most of the formulations were mixed in the laboratory for expedience of changing formulations, some cushions were produced using a conventional mix/meter machine (e.g., Edge Sweets Foam Machine Model Flex-2H, Grand Rapids, Mich.). When using the foam machine it was discovered that cushions could be made, colored and/or coated for much less than with the processes used to make virtually all of the noise excluding earmuffs on the market today.

Currently, commercial earmuff cushions are made using a minimum of two thin sheets of polyvinyl chloride or polyurethane, one of which is vacuum formed and filled with a cut-out donut of foam or a liquid followed by thermal bonding and cutting off the trim. Because of the low volumes normally employed, the process is labor intense, results in considerable waste and is costly.

Results

Formulations and testing results for earmuff cushions are shown in Table 1. Examination of the data in Table 1 indicates that both cushion 11 and cushion 15 are good performers. It should be noted that Example formulation 15 cushions of the Standard size yields the highest insertion loss for that size. This along with comparative results for the cushions from Example 14 in the Standard, Medium & Thin sizes leads one to believe that the thickness as worn preferably should be less than 0.5 inch.

Figure 12:
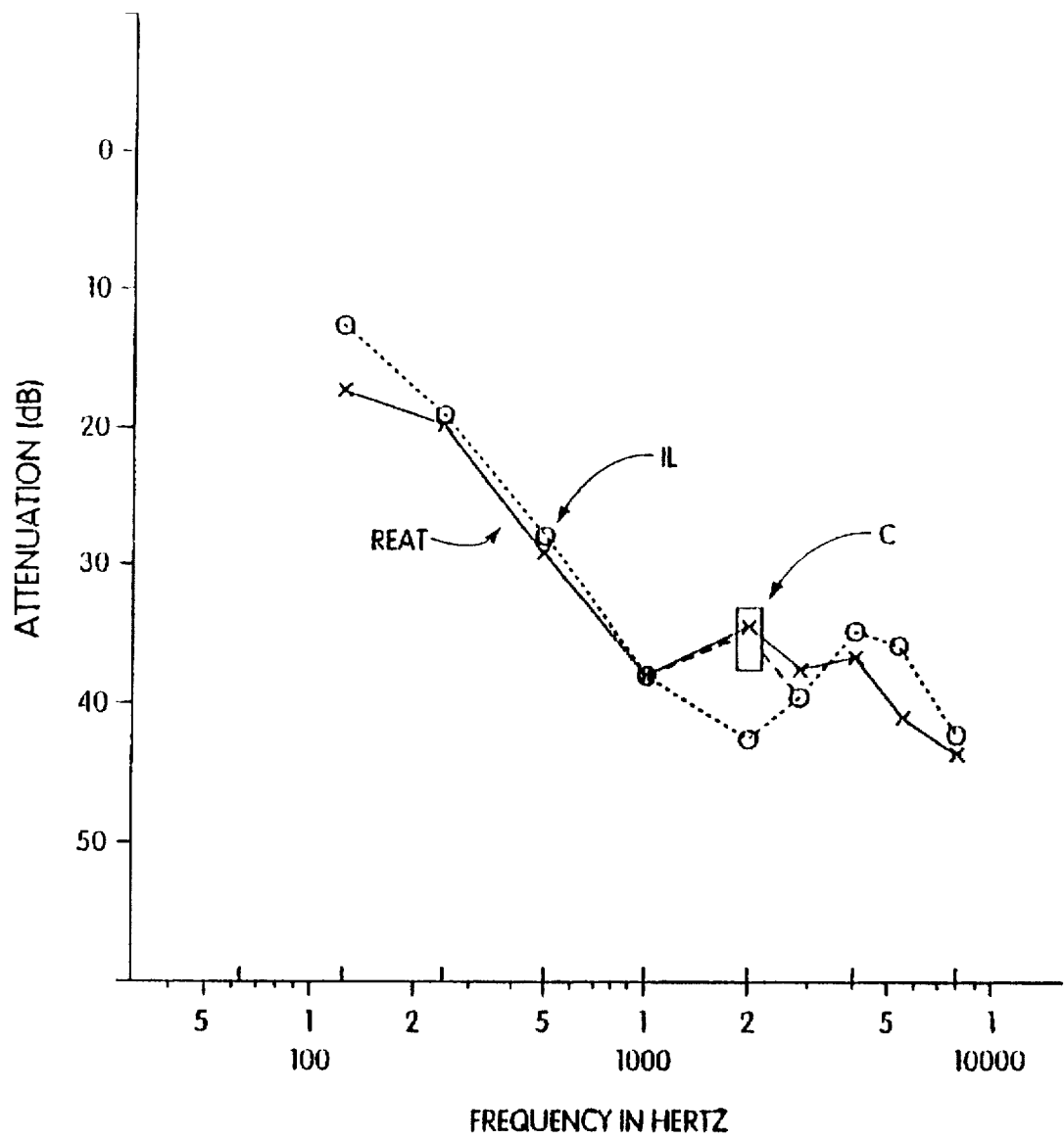
FIG. 12 shows a comparison of REAT and IL values as a function of frequency for an earmuff.

Four earmuff cushions were selected for Real-Ear Attenuation Testing at Threshold (REAT) by ANSI S3.19 and comparison made of those attenuation results with insertion loss values. All attenuation results were in conformance with ANSI S3.19 except that five subjects were employed. FIG. 12 shows the comparison of REAT to IL values as a function of frequency for Model 1000 Earmuffs with dynamically stiff cushions, Example 11 (Std.). This figure shows the IL (calculated NRR=22) vs. REAT (NRR=24) comparison for Model 1000 ear muffs with dynamically stiff cushions of example 11. The bone conduction limited area is shown as C. These cushions were selected to be close to but superior to Normal Model 1000 cushions.

FIG. 13 shows the comparison of REAT (NRR=25) to IL values (calculated NRR=25 as a function of frequency for Model 1000 Earmuffs with dynamically stiff cushions of Example 5 (Std.). C is the bone conduction limited area. These cushions were selected as having close to marginal static deflection for problem subjects.

Figure 14:
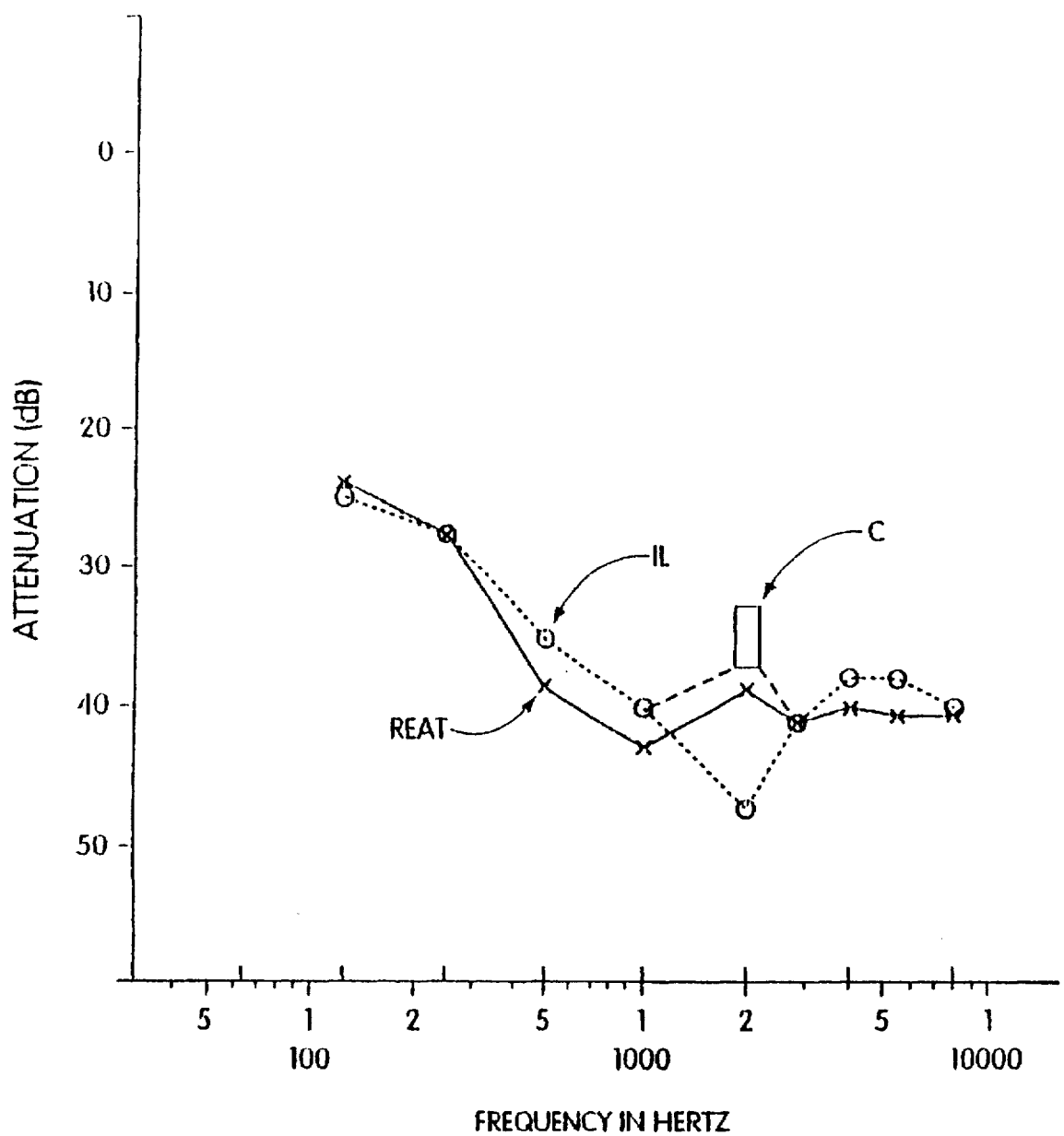
FIG. 14 shows a comparison of REAT to IL values as a function of frequency for earmuffs.

FIG. 14 shows the comparison of REAT (NRR=29) to IL values (calculated NRR=29) as a function of frequency for Model 3000 Earmuffs with dynamically stiff cushions of Example 14 (Med.). The bone conduction limited area is shown as C. These cushions were selected because of their superior IL performance on Model 3000 Earmuffs.

Figure 15:
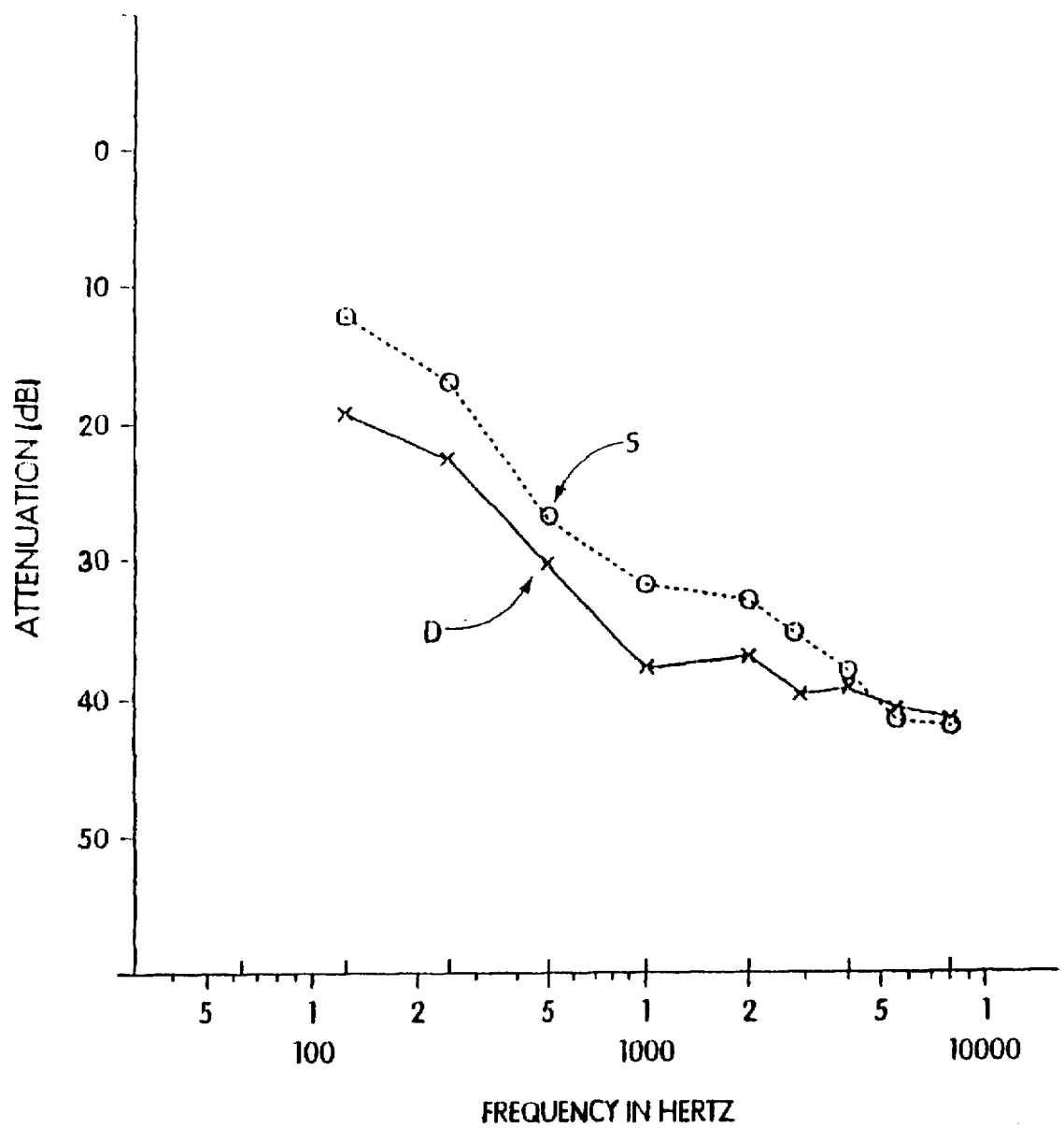
FIG. 15 shows REAT comparisons.

FIG. 15 shows a REAT comparison for Model 1000 Earmuffs having dynamically stiff cushions (D) of Example 15 (Med.)(NRR=25) as compared to the same earmuffs having their normal cushions (S) (NRR=20).

Figure 16:
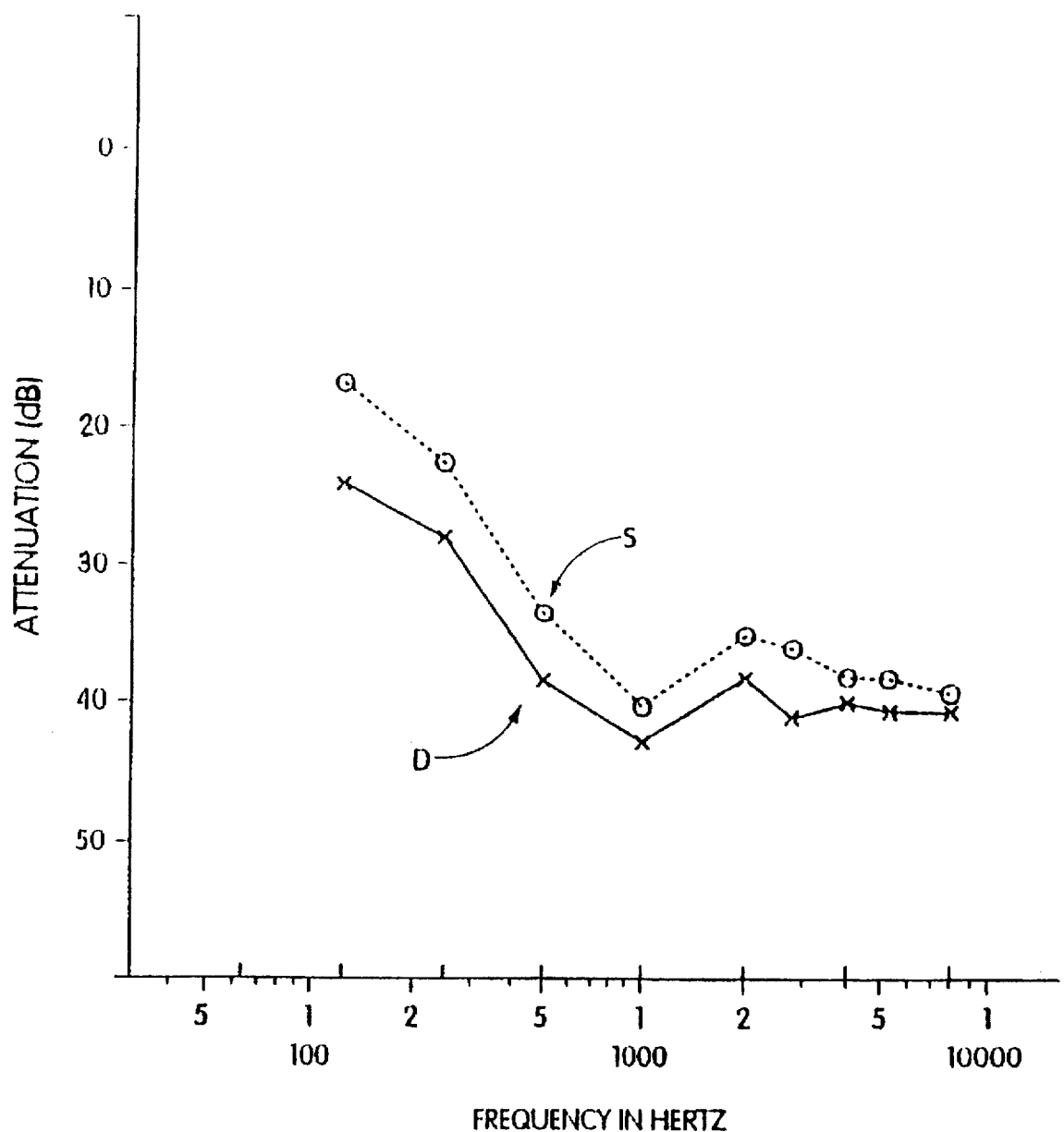
FIG. 16 shows REAT comparisons.

FIG. 16 shows a REAT comparison for Model 3000 Earmuffs having dynamically stiff cushions (D) (NRR=29) of Example 14 (Med.) as compared to the same earmuffs having their normal cushions (S) (NRR=25).

All of these results from FIG. 11 through FIG. 16 show the close correlation between REAT and IL and the superior performance of dynamically stiff earmuff cushions over normal earmuff cushions.

Coatings

Finally, sample earmuff cushions were coated with an in-mold aliphatic sky blue polyurethane, Aliphlex MPM-E180A. The coating was applied in-mold (spraying the mold, 10% solids composition, approximately one mil thick) prior to foam formulation addition (can also be applied alternately to the foam cushion after production). Both coatings were reasonable with the in-mold coating having superior looks and feel. The cushions spray-coated after production resulted in some absorption into the surface. Insertion loss test results indicated that coated cushions yield the same improved low frequency attenuation and estimated NRRs as the uncoated dynamically stiff cushions.

In addition to the above-described tests performed on foam cushions for earmuffs, attenuation tests were performed for foam pod components of semi-aural hearing protectors according to Examples 23 and 24. In particular, attenuation tests were performed for foam pod components of semi-aural hearing protectors, of the type which enters the ear canal and seals the ear canal prior to the bend. It was noticed that occasional subjects have difficulty fitting earplugs and semi-aural devices. It was believed that earplugs or semi-aural devices that fit such subjects, yielding good attenuation, would be superior hearing protective devices capable of protecting a greater range of potential users. Thus, a particular individual, Fields, was selected for testing based on his difficulty in fitting push-in earplugs and semi-aural devices.

To explain why Fields was difficult to fit, anthropometric measurements of thirty subject's ear canals were made, form ear molds of the subjects' ear canals. Fields' left ear canal measured only 0.187 inches (4.75 mm) at its narrowest point prior to the bend in the ear canal. The width when measured at the point where the ear canal was the narrowest measured 0.447 inches (11.35 mm), thus yielding an aspect ratio of 2.39. These dimensions probably explain why Fields is difficult to fit with earplugs or semi-aural devices.

The foam pod components were therefore tested for attenuation in accordance with ANSI S3.19 with Fields as the only subject. The foam pods were attached to the neckband of FIG. 17A, suing a short section of vinyl tubing so as to allow ease of rotation of the tubing about the balls 36 at each end of neckband 30. The results are shown in the Table below:

Example 23

| Attenuation | As Received | With Pond's Cold Cream | Example 24 As Received |
| --- | --- | --- | --- |
| 125 Hz | 30.7 | 36.3 | 35.3 |
| 250 Hz | 25.3 | 31.0 | 33.7 |
| 500 Hz | 19.3 | 33.3 | 38.0 |
| 1000 Hz | 22.7 | 36.3 | 39.7 |
| 2000 Hz | 28.3 | 31.3 | 34.0 |
| 3150 Hz | 40.3 | 39.0 | 43.0 |
| 4000 Hz | 40.3 | 39.0 | 40.7 |
| 6300 Hz | 43.3 | 49.0 | 44.7 |
| 8000 Hz | 43.3 | 49.0 | 44.7 |
| NRR, dB | 18.9 | 27.3 | 27.7 |
| Comfort | 3 | 3 | 3 |

Figure 23:
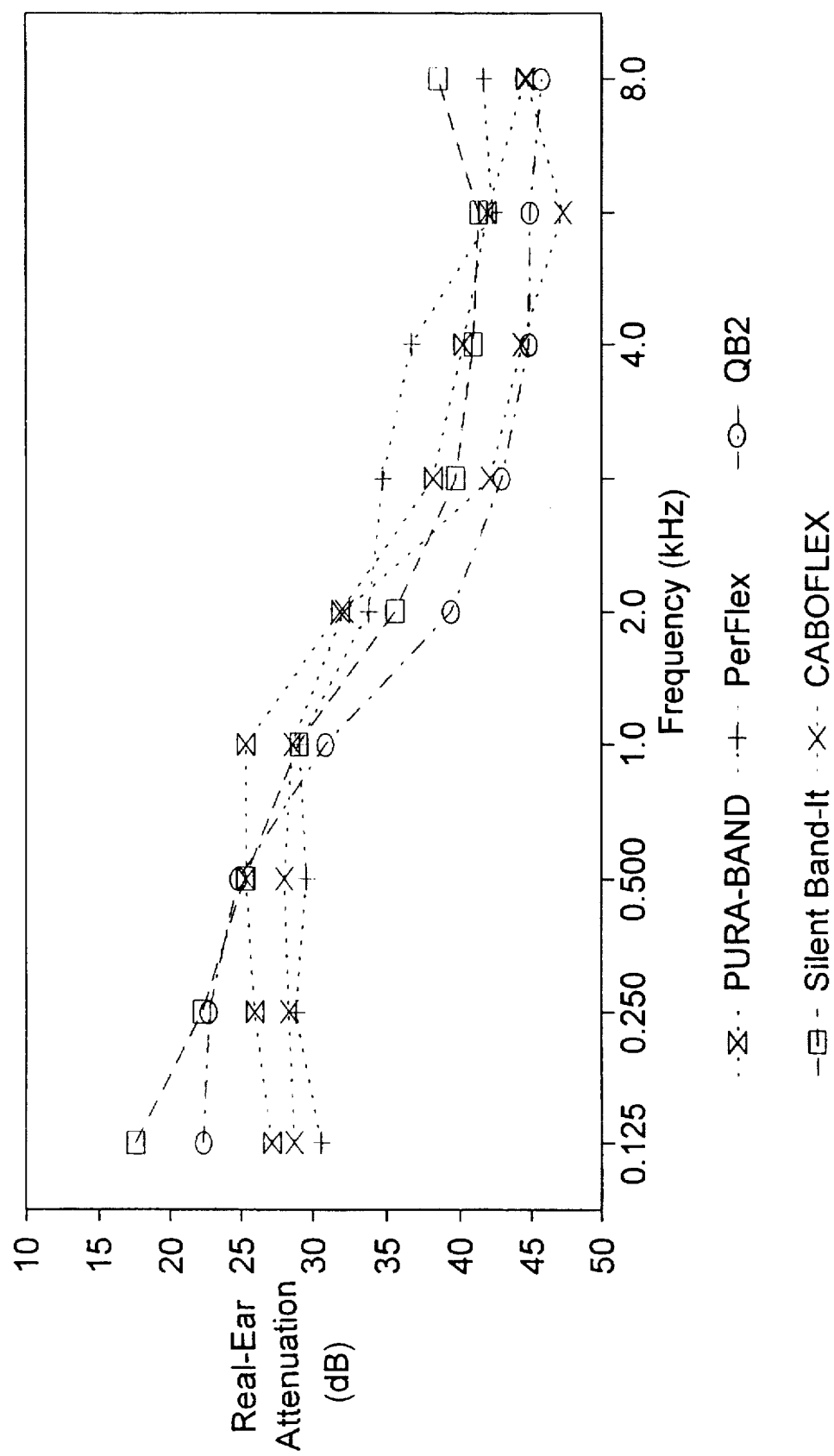
FIG. 23 shows attenuation of semi-aural bearing protectors of the prior art which enter the ear canal.
Figure 24:
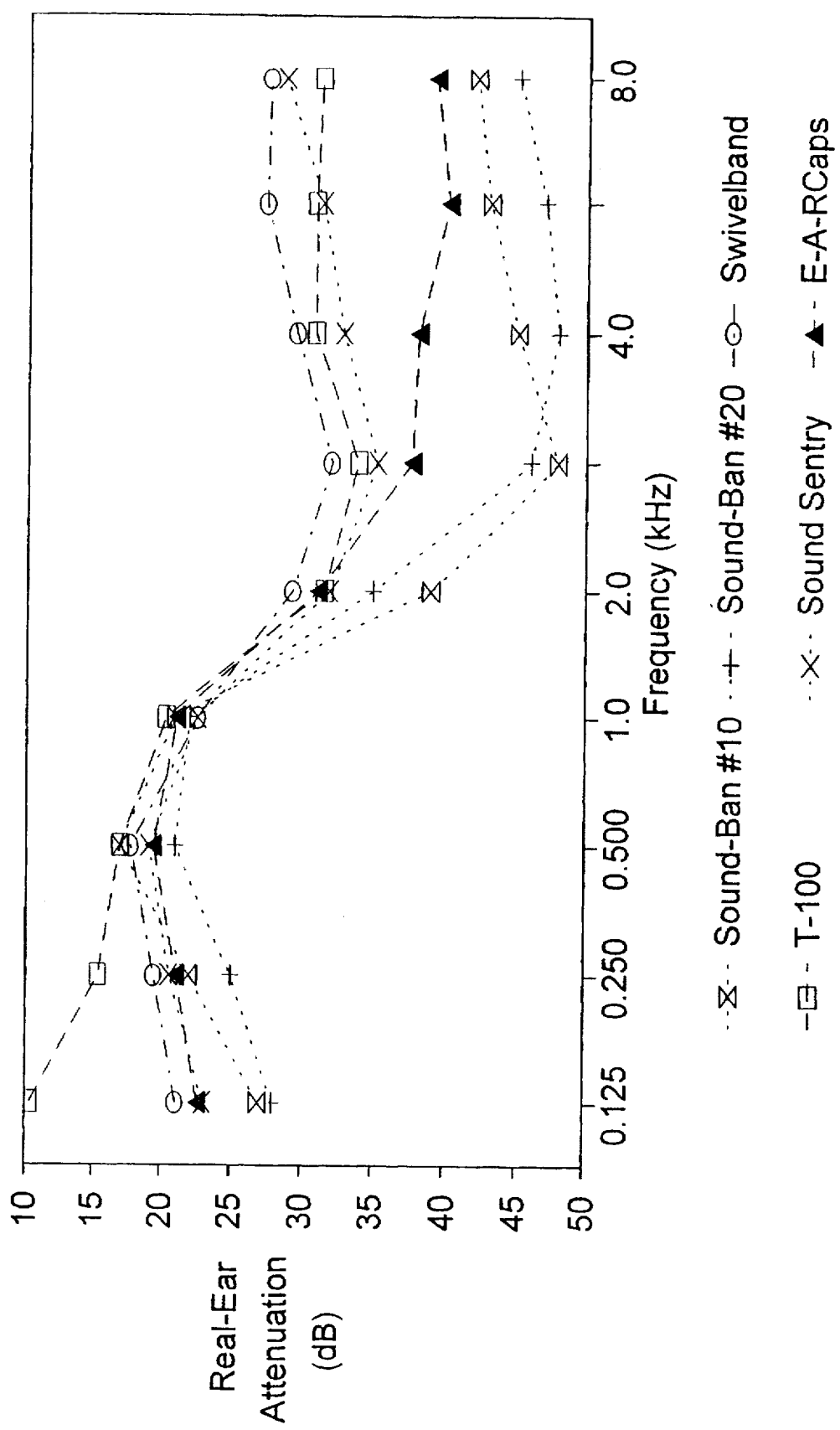
FIG. 24 shows attenuation of semi-aural protectors of the prior art which cap the ear.

As shown in the above Table, a slippery surface (in this test produced by the application of Pond's cold cream) aids insertion, allowing much improved attenuation. Furthermore, the stem, which functions as a stiffener, allows the fabrication of semi-aural devices yielding attenuation on a difficult-to-fit subject exceeding reported attenuations of all other semi-aural devices shown in FIGS. 23 and 24. Finally, Example 24, which has pods of dynamically stiff foam without a slippery surface, yields even higher low frequency attenuation results. Here again, the stem, acting a stiffener, is an important element of the semi-aural device.

In addition to increased attenuation, the earmuff cushions, semi-aural device components and earplugs of the present invention provide improved ease of manufacture. Many earmuff cushions have been made and tested, most of which gave superior low frequency insertion loss and estimated NRRs. REAT and IL values as well as NRRs calculated from them checked each other very well although if questions should arise REAT ANSI S3.19 values could be utilized as a reference. All foam cushions produced of molded polyurethane on foam machinery have an ease of manufacturing advantage (which would also show itself as a low cost manufacturing advantage). Cushions having static deflections of about 0.05 inch or greater are preferred for problem subjects with a static deflection of about 0.10 or more being more preferred. Cushions having an Fn as tested in this report of about 52 Hz or more show equal to or superior performance to normal cushions. Cushion which deflect to a thickness of about 0.5 inch or less when compressed (as measured by the static deflection test) are preferred. Cushions with increased contact with the head are preferred. An example of this is the reversed taper shape referred to in FIG. 11 although other thicknesses are certainly applicable.

Applied coatings, especially in-mold coatings, may be advantageous. Placing molded dynamically stiff cushions into current art bladders may also yield increased performance but at higher cost. The total effect of amplification at resonance (A) is not totally understood at this time. It is felt that cushions having Fn about 52 Hz or less may be useable as low cost cushions of similar performance to the prior art. However, more highly resilient cushions having Fn of about 52 Hz or less with A of 9.5 dB or more may yield inferior attenuation.

From the above, it can be seen that as tested, the cushions of the present invention results in at least a 3 to 4 dB increase in attenuation over that obtainable with a conventional earmuff cushion. In addition, the cushion of the present invention is easier to manufacture than conventional muffs. For example, in addition of the elimination of a bladder, it can be formed directly onto a cushion seal end plate, if desired. The dynamically stiff foam and method of manufacture of the present invention are also expected to provide improved components for various semi-aural devices, as well as for earplugs and other hearing protective devices.

What is claimed is:

1. A semi-aural hearing protector comprising:
   a generally U-shaped connecting band; and
   a pair of pods fastened to opposite ends of the generally U-shaped connecting band, the pods having a forward portion for contact with the ear of a wearer and comprising a dynamically stiff foam component for contact with the ear of the wearer, wherein the foam component has a low static stiffness and a high dynamic stiffness, resulting in the semi-aural device having higher sound attenuation; and wherein the foam component has a dynamic spring constant of at least about 300 pounds per inch and a dynamic loss factor of at least about 0.25.

2. The semi-aural hearing protector of claim 1, wherein the foam component has a dynamic spring constant of at least about 1,000 pounds per inch.

3. The semi-aural hearing protector of claim 1, wherein the foam component has a static spring constant of up to about 60 pounds per inch.

4. The semi-aural hearing protector of claim 1, wherein the foam component has a static spring constant of up to about 30 pounds per inch.

5. The semi-aural hearing protector of claim 1, wherein the foam component comprises a polyurethane.

6. The semi-aural hearing protector of claim 5, wherein the polyurethane is the reaction product of a diisocyanate and a polyol component, the resulting polyurethane having an isocyanate index of less than about 0.9.

7. The semi-aural hearing protector of claim 6, wherein the polyol component further comprises at least one additive selected from the group consisting of latex, oils, catalysts, fillers, plasticizers, colorants, antifoam agents, surfactants, fire retardants, cell stabilizers, cell regulators, chain extenders, hindered amine light stabilizers and internal mold release agents.

8. The semi-aural hearing protector of claim 5, wherein the polyol component comprises at least one polyol, and wherein at least a portion of the polyol component has a functionality of at least three.

9. The semi-aural hearing protector of claim 1, wherein the foam component further comprises a coating to aid insertion into the ear of a wearer, the coating being applied as an in-mold coating or a coating applied after removal of the foam from the mold.

10. The semi-aural hearing protector of claim 1, wherein the foam component is encapsulated.

11. The semi-aural hearing protector of claim 1, further comprising a stiffener having a tip portion, wherein at least the tip portion of the stiffener is disposed within the foam component.

12. The semi-aural hearing protector of claim 11, wherein the tip of the stiffener has increased bendability.

13. The semi-aural hearing protector of claim 11, wherein the forward portion of the foam component that is ahead of the stiffener is at least about 0.25 inches long and the cross-section of the foam component at the tip of the stiffener is at least about 0.46 inches in diameter.

14. The semi-aural hearing protector of claim 1 having a bore extending through the foam component, said bore being adapted to receive sound.

15. The semi-aural hearing protector of claim 1, further comprising a transceiver embedded in the foam component, and having a bore extending from the forward portion of the pod to the transceiver, said bore being adapted to transmit sound from the transceiver to the wearer.

16. A semi-aural hearing protector comprising:

a generally U-shaped connecting band; and a pair of pods fastened to opposite ends of the generally U-shaped connecting band, the pods having a forward portion for contact with the ear of a wearer and comprising a foam component for contact with the ear of the wearer, and a stiffener at least partially disposed within the foam component such that the stiffener pulls the foam component into the ear upon insertion to maximize attenuation.

17. The semi-aural hearing protector of claim 16, wherein the foam component further comprises a polyurethane coating to aid insertion into the ear of the wearer, the coating being applied as an in-mold coating or a coating applied after removal of the foam from the mold.

18. The semi-aural hearing protector of claim 16, wherein the foam component is encapsulated.

19. The semi-aural hearing protector of claim 16, wherein the stiffener includes a tip portion, wherein at least the tip portion of the stiffener is disposed within the foam component and the tip portion has increased bendability.

20. The semi-aural hearing protector of claim 16, wherein the forward portion of the foam component that is ahead of the stiffener is at least about 0.25 inches long and the cross-section of the foam component at the tip of the stiffener is at least about 0.46 inches in diameter.

21. A foam component for a semi-aural hearing protector wherein:

the foam component has a low static stiffness and a high dynamic stiffness, resulting in the semi-aural device having higher sound attenuation;

the foam component has a dynamic spring constant of at least about 300 pounds per inch and a dynamic loss factor of at least about 0.25; and the foam component having a forward portion for contact with the ear.

22. The foam component of claim 21, wherein the foam has a dynamic spring constant of at least about 1,000 pounds per inch.

23. The foam component of claim 21, wherein the foam has a static spring constant of up to about 60 pounds per inch.

24. The foam component of claim 22, wherein the foam has a static spring constant of up to about 30 pounds per inch.

25. The foam component of claim 23, wherein the foam comprises a polyurethane.

26. The foam component of claim 24, wherein the polyurethane is the reaction product of a diisocyanate and a polyol component, the resulting polyurethane having an isocyanate index of less than about 0.9.

27. The foam component of claim 26, wherein the polyol component further comprises at least one additive selected from the group consisting of latex, oils, catalysts, fillers, plasticizers, colorants, antifoam agents, surfactants, fire retardants, cell stabilizers, cell regulators, chain extenders, hindered amine light stabilizers and internal mold release agents.

28. The foam component of claim 25, wherein the polyol component comprises at least one polyol, and wherein at least a portion of the polyol component has a functionality of at least three.

29. The foam component of claim 21, further comprising a polyurethane coating to aid insertion into the ear, the coating being applied as an in-mold coating or a coating applied after removal of the foam from the mold.

30. The foam component of claim 21, wherein the foam component is encapsulated.

31. The foam component of claim 21, further comprising a stiffener having a tip portion, wherein at least the tip portion of the stiffener is disposed within the foam component.

32. The foam component of claim 31, wherein the tip of the stiffener has increased bendability.

33. The foam component of claim 31, wherein the forward portion of the foam component ahead of the stiffener is at least about 0.25 inches long and the cross-section of the foam component at the tip of the stiffener is at least about 0.46 inches in diameter.

34. The foam component of claim 21 having a bore extending through the foam component, said bore being adapted to receive sound.

35. The foam component of claim 21, further comprising a transceiver embedded in the foam component, and having a bore extending from the forward portion of the foam component to the transceiver, said bore being adapted to transmit sound from the transceiver to the wearer.

36. A pod having a forward pod portion for contact with the wearer's ear for a semi-aural hearing protector comprising a foam component having a rearward portion and a forward foam portion for insertion into a wearer's ear canal; and a stiffener having a tip portion, wherein at least the tip portion is at least partially disposed within the foam component and the stiffener extends outwardly from the rearward portion of the foam component, the tip portion having increased bendability.

37. The pod of claim 36, wherein the foam component further comprises a polyurethane coating to aid insertion into the ear of the wearer, the coating being applied as an in-mold coating or a coating applied after removal of the foam from the mold.

38. The pod of claim 36, wherein the forward portion of the foam component that is ahead of the stiffener is at least about 0.25 inches long and the cross-section of the foam component at the tip of the stiffener is at least about 0.46 inches in diameter.

39. An earplug hearing protector comprising a dynamically stiff foam component having a forward portion for contact with the ear of the wearer, wherein:

the foam has a low static stiffness and a high dynamic stiffness, resulting in the earplug having higher sound attenuation; and a dynamic spring constant of at least about 300 pounds per inch and a dynamic loss factor of at least about 0.25.

40. The earplug of claim 39, wherein the foam has a dynamic spring constant of at least about 1,000 pounds per inch.

41. The earplug of claim 39, wherein the foam has a dynamic spring constant of at least about 1,000 pounds per inch and a dynamic material loss factor of at least about 0.25.

42. The earplug of claim 39, wherein the foam has a static spring constant of up to about 60 pounds per inch.

43. The earplug of claim 39, wherein the foam has a static spring constant of up to about 30 pounds per inch.

44. The earplug of claim 39, wherein the foam component is comprised of a polyurethane.

45. The earplug of claim 39, wherein the polyurethane is the reaction product of a diisocyanate and a polyol component, the resulting polyurethane having an isocyanate index of less than about 0.9.

46. The earplug of claim 44, wherein the polyol component comprises at least one polyol, and wherein at least a portion of the polyol component has a functionality of at least three.

47. The earplug of claim 45, wherein the polyol component further comprises at least one additive selected from the group consisting of latex, oils, catalysts, fillers, plasticizers, colorants, antifoam agents, surfactants, fire retardants, cell stabilizers, cell regulators, chain extenders, hindered amine light stabilizers and internal mold release agents.

48. The earplug of claim 39, wherein the foam component further comprises a polyurethane coating to aid insertion into the ear of the wearer, the coating being applied as an in-mold coating or a coating applied after removal of the foam from the mold.

49. The earplug of claim 39, wherein the foam component is encapsulated.

50. The earplug of claim 39, further comprising a stiffener having a tip portion, wherein at least the tip portion is partially disposed within the foam component.

51. The earplug of claim 50, wherein the tip of the stiffener disposed within the foam component has increased bendability.

52. The earplug of claim 50, wherein the forward portion of the foam component ahead of the stiffener is at least about 0.25 inches long and the cross-section of the foam component at the tip of the stiffener is at least about 0.46 inches in diameter.

53. The earplug of claim 39 having a bore extending through the foam component, said bore being adapted to receive sound.

54. The earplug of claim 39, further comprising a transceiver embedded in the foam component, and having a bore extending from the forward portion of the foam component to the transceiver, said bore being adapted to transmit sound from the transceiver to the wearer.

55. An earplug comprising a foam component, wherein the foam component has a forward portion for contact with a wearer's ear; and a stiffener having a tip portion of increased bendability, wherein at least the tip portion of the stiffener is at least partially disposed within the foam component such that the stiffener pulls the foam component into the ear during insertion to maximize attenuation, and further wherein the forward portion of the foam component ahead of the stiffener is at least about 0.25 inches long and the cross-section of the foam component at the tip of the stiffener is at least about 0.46 inches in diameter.

56. The earplug of claim 55, wherein the foam component further comprises a coating to aid insertion into the ear, the coating being applied as an in-mold coating or a coating applied after removal of the foam from the mold.

57. The earplug of claim 55, wherein the foam component is encapsulated.

\* \* \* \* \*

UNITED STATES PATENT AND TRADEMARK OFFICE
CERTIFICATE OF CORRECTION

PATENT NO. : 5,792,998
DATED : August 11, 1998
INVENTOR(S) : Ross Gardner, Jr. et al.

It is certified that error appears in the above-indentified patent and that said Letters Patent is hereby corrected as shown below:

In Column 1, Line 10 delete "08/450, 122 filed Oct. 6, 1995 now abandoned" and insert therefor --08/540, 122 filed May 25, 1995--
In Column 1, Line 23 delete "08/450, 122, now abandoned" and insert therefor --08/450,122--
In Column 3, Line 32 delete "form" and insert therefor --from--
In Column 10, Line 42 insert a period --.-- between "therefor" and "The"
In Table 1, Under Physical Properties delete "Fa(lbs/inch)" and insert therefor --Fs (lbs/inch)--
In Table 1, Under Column labled "Sample 9" Line PPG-425 delete "12.90" and insert therefor --12.00--
In Table 1, Under Physical Properties, delete "Ka (lbs/inch)" and insert therefor --Ks(lbs/inch)--
In Table 1, Under Transmissibility delete "K (lbs/inch)" and insert therefor --K* (lbs/inch)--
In Column 21, Line 61 insert --)-- between "25" and "as"
In Column 22, Line 64 delete "suing" and insert therefor --using--
In Column 23, Line 26 insert therefor --as-- between "acting" and "a"
In Column 23, Line 44 delete "Cushion" and insert therefor --Cushions--

Signed and Sealed this

Tenth Day of April, 2001

*Attest:*

NICHOLAS P. GODICI

*Attesting Officer*     *Acting Director of the United States Patent and Trademark Office*